United States Patent
Phillips et al.

(10) Patent No.: US 10,898,570 B2
(45) Date of Patent: Jan. 26, 2021

(54) COMBINATION THERAPY WITH AN ANTI-HER2 ANTIBODY-DRUG CONJUGATE AND A BCL-2 INHIBITOR

(71) Applicant: Genentech, Inc., South San Francisco, CA (US)

(72) Inventors: Gail Lewis Phillips, South San Francisco, CA (US); Deepak Sampath, South San Francisco, CA (US); Ingrid Wertz, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/849,018

(22) Filed: Dec. 20, 2017

(65) Prior Publication Data

US 2018/0140700 A1 May 24, 2018

Related U.S. Application Data

(63) Continuation of application No. PCT/US2016/041184, filed on Jul. 6, 2016.

(60) Provisional application No. 62/189,610, filed on Jul. 7, 2015.

(51) Int. Cl.
| | |
|---|---|
| A61K 39/395 | (2006.01) |
| C07K 16/32 | (2006.01) |
| G01N 33/574 | (2006.01) |
| A61K 47/68 | (2017.01) |
| A61K 31/635 | (2006.01) |
| A61K 45/06 | (2006.01) |
| A61P 35/00 | (2006.01) |
| A61K 31/496 | (2006.01) |
| A61K 39/00 | (2006.01) |

(52) U.S. Cl.
CPC ...... *A61K 39/39558* (2013.01); *A61K 31/496* (2013.01); *A61K 31/635* (2013.01); *A61K 45/06* (2013.01); *A61K 47/6803* (2017.08); *A61K 47/6809* (2017.08); *A61K 47/6851* (2017.08); *A61P 35/00* (2018.01); *C07K 16/32* (2013.01); *G01N 33/57415* (2013.01); *G01N 33/57446* (2013.01); *A61K 2039/505* (2013.01); *A61K 2300/00* (2013.01); *C07K 2317/24* (2013.01); *C07K 2317/73* (2013.01); *G01N 2333/4703* (2013.01); *G01N 2800/52* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 5,202,238 A | 4/1993 | Fell, Jr. et al. |
| 5,204,244 A | 4/1993 | Fell et al. |
| 5,208,020 A | 5/1993 | Chari et al. |
| 5,677,171 A | 10/1997 | Hudziak et al. |
| 5,821,337 A | 10/1998 | Carter et al. |
| 6,054,297 A | 4/2000 | Carter et al. |
| 6,165,464 A | 12/2000 | Hudziak et al. |
| 6,339,142 B1 | 1/2002 | Basey et al. |
| 6,407,213 B1 | 6/2002 | Carter et al. |
| 6,441,163 B1 | 8/2002 | Chari et al. |
| 6,639,055 B1 | 10/2003 | Carter et al. |
| 6,719,971 B1 | 4/2004 | Carter et al. |
| 6,790,954 B2 | 9/2004 | Chung et al. |
| 6,800,738 B1 | 10/2004 | Carter et al. |
| 7,074,404 B2 | 7/2006 | Basey et al. |
| 7,097,840 B2 | 8/2006 | Erickson et al. |
| 8,663,643 B2 * | 3/2014 | Berry ................ A61K 31/5377 424/181.1 |
| 2005/0166993 A1 | 8/2005 | Viken et al. |
| 2005/0170475 A1 | 8/2005 | Kuo et al. |
| 2005/0276812 A1 | 12/2005 | Ebens, Jr. et al. |
| 2010/0305122 A1 | 12/2010 | Bruncko et al. |
| 2014/0086940 A1 | 3/2014 | Bryant |

FOREIGN PATENT DOCUMENTS

| | | |
|---|---|---|
| CN | 104370905 A | 2/2015 |
| WO | WO 1999/060023 A1 | 11/1999 |
| WO | WO 01/00244 | 1/2001 |
| WO | WO 02/17852 | 3/2002 |
| WO | WO 2004/056971 A2 | 7/2004 |
| WO | WO 2009/117277 A2 | 9/2009 |
| WO | WO 2010/138588 A2 | 12/2010 |
| WO | WO 2012/071336 | 5/2012 |
| WO | WO 2012/154809 | 11/2012 |

OTHER PUBLICATIONS

Milella et al. ("Milella", Clin. Cancer Res. 2004, 10, 7747-7756) (Year: 2004).*
Carpenter et al. ("Carpenter", J. Carcinog. Mutagen, 2013, 1-13) (Year: 2013).*
Abulwerdi et al., "3-Substituted-N-(4-Hydroxynaphthalen-1-yl)arylsulfonamides as a Novel Class of Selective Mcl-1 Inhibitors: Structure-Based Design, Synthesis, SAR, and Biological Evaluation," J. Med. Chem. 57:4111-4133 (2014).
Abulwerdi et al., "A Novel Small-Molecule Inhibitor of Mcl-1 Blocks Pancreatic Cancer Growth In Vitro and In Vivo," Mol Cancer Ther 13(3):565-575 (2013).
Adams, "Ways of dying: multiple pathways to apoptosis," Genes & Development 17:2481-2495 (2003).
Nicolaou et al., "Calicheamicin $\theta^1$: A Rationally Designed Molecule with Extremely Potent and Selective DNA Cleaving Properties and Apoptosis Inducing Activity," Angew Chem. Intl. Ed. Engl. 33(2):183-186 (1994).

(Continued)

*Primary Examiner* — Lei Yao
(74) *Attorney, Agent, or Firm* — Baker Botts L.L.P.

(57) ABSTRACT

The present invention is directed to a combination therapy involving an anti-HER2 antibody-drug conjugate and a selective Bcl-2 inhibitor for the treatment of a patient suffering from cancer, particularly, a HER2-expressing cancer.

6 Claims, 22 Drawing Sheets

Specification includes a Sequence Listing.

(56) References Cited

OTHER PUBLICATIONS

Antibodies, A Laboratory Manual, Cold Spring Harbor Laboratory, Ed Harlow and David Lane (1988).
Antonsson et al., "Bax Is Present as a High Molecular Weight Oligomer/Complex in the Mitochondrial Membrane of Apoptotic Cells," Journal of Biological Chemistry 276(15):11615-11623 (2001).
Baselga et al, "Phase II Study of Weekly Intravenous Recombinant Humanized Anti-p18HER2 Monoclonal Antibody in Patients with HER2/neu-Overexpressing Metastatic Breast Cancer," J. Clin. Oncol. 14:737-744 (1996).
Baselga et al., "Recombinant Humanized Anti-HER2 Antibody (HerceptinTM) Enhances the Antitumor Activity of Paclitaxel and Doxorubicin against HER2/neu Overexpressing Human Breast Cancer Xenografts," Cancer Res. 58:2825-2831 (1998).
Beeram et al., "A Phase 1 Study of Weekly Dosing of Trastuzumab Emtansine (T-DM1) in Patients with Advanced Human Epidermal Growth Factor 2-Positive Breast Cancer," Cancer 118:5733-5740 (2012).
Belmar et al., "Small molecule Mcl-1 inhibitors for the treatment of cancer," Pharmacology & Therapeutics 145:76-84 (2015).
Bruncko et al., "Structure-Guided Design of a Series of MCL-1 Inhibitors with High Affinity and Selectivity," J. Med. Chem. 58:2180-2194 (2015).
Burke et al., "Discovery of Tricyclic Indoles That Potently Inhibit Mcl-1 Using Fragment-Based Methods and Structure-Based Design," J. Med. Chem. 58(9):3794-3805 (2015).
Cabanillas et al., "Results of a Phase II Study of Maytansine in Patients with Breast Carcinoma and Melanoma," Cancer Treat Rep, 63:507-509 (1979).
Cartron et al., "The First α Helix of Bax Plays a Necessary Role in Its Ligand-Induced Activation by the BH3-Only Proteins Bid and PUMA," Mol Cell 16:807-818 (2004).
Cassady et al., "Recent Developments in the Maytansinoid Antitumor Agents," Chem Pharm Bull 52(1):1-26 (2004).
Cheng et al., "BCL-2, BCL-XLSequester BH3 Domain-Only Molecules Preventing BAX- and BAK-Mediated Mitochondrial Apoptosis," Molecular Cell 8:705-711 (2001).
Chothia et al., "Canonical Structures for the Hypervariable Regions of Immunoglobulins," J. Mol. Biol. 196:901-917 (1987).
Chou et al., "Quantitative Analysis of Dose-Effect Relationships: The Combined Effects of Multiple Drugs or Enzyme Inhibitors," Adv. Enzyme Regul. 22:27-55 (1984).
Cory et al., "The BCL2 Family: Regulators of the Cellular Life-Or-Death Switch," Nature Reviews Cancer 2:647-656 (2002).
Coussens et al., "Tyrosine Kinase Receptor with Extensive Homology to EGF Receptor Shares Chromosomal Location with neu Oncogene," Science 230:1132-1139 (1985).
Crawford et al., "Targeting Bcl-2 in Herceptin-Resistant Breast Cancer Cell Lines," Current Pharmacogenomics & Personalized Medicine, 9:184-190 (2011).
Danial et al., "Cell Death: Critical Control Points," Cell 116:205-219 (2004).
Franklin et al., "Insights into ErbB signaling from the structure of the ErbB2-pertuzumab complex," Cancer Cell 5:317-328 (2004).
Friberg et al., "Discovery of potent myeloid cell leukemia 1 (Mcl 1) inhibitors using fragment-based methods and structure-based design," J. Med. Chem. 56:15-30 (2013).
Green et al., "The Pathophysiology of Mitochondrial Cell Death," Science 305:626-629 (2004).
Hanna et al., "HER2 in situ hybridization in breast cancer: clinical implications of polysomy 17 and genetic heterogeneity," Modern Pathology 27:4-18 (2014).
Hotaling et al., [abstract]. Proc. Annual Meeting Am Assoc Cancer Res; 37:471 (1996).
Hsu et al., "Cytosol-to-membrane redistribution of Bax and Bcl-XL during apoptosis," PNAS 94:3668-3672 (1997).
Hsu et al., "Nonionic Detergents Induce Dimerization among Members of the Bcl-2 Family," Journal of Biological Chemistry 272(21):13829-13834 (1997).
Huang et al., "BH3-Only Proteins—Essential Initiators Minireview of Apoptotic Cell Death," 103:839-842 (2000).
Hudziak et al., "p185HER2 Monoclonal Antibody Has Antiproliferative Effects In Vitro and Sensitizes Human Breast Tumor Cells to Tumor Necrosis Factor," Mol. Cell Biol 9(3):1165-1172 (1989).
International Search Report dated Nov. 3, 2016 in International Application No. PCT/US2016/041184.
Issell et al., "Maytansine," Cancer Treat. Rev. 5:199-207 (1978).
Kabat et al., Sequences of Proteins of Immunological Interest, 5th Ed. Public Health Service, National Institutes of Health, Bethesda, MD (1991).
Kellermann et al., "Antibody discovery: the use of transgenic mice to generate human monoclonal antibodies for therapeutics," Curr Opin Biotechnol. 13:593-597 (2002).
Kindt et al., Kuby Immunology, 6th ed., W.H. Freeman and Co., p. 91 (2007).
Koehler et al., "Structure-Guided Rescaffolding of Selective Antagonists of BCL-XL," ACS Med. Chem. Lett. 5:662-667 (2014).
Krop et al., "A Phase II Study of Trastuzumab Emtansine in Patients with Human Epidermal Growth Factor Receptor 2-Positive Metastatic Breast Cancer Who Were Previously Treated with Trastuzumab, Lapatinib, an Anthracycline, a Taxane, and Capecitabine," Journal of Clinical Oncology 30(26):3234-3241 (2012).
Krop et al., "Phase I Study of Trastuzumab-DM1, an HER2 Antibody-Drug Conjugate, Given Every 3 Weeks to Patients with HER2-Positive Metastatic Breast Cancer," J. Clin. Oncol. 28(16):2698-2704 (2010).
Kuwana et al., "Bid, Bax, and Lipids Cooperate to Form Supramolecular Openings in the Outer Mitochondrial Membrane," Cell 111:331-342 (2002).
Lambert et al., "Ado-trastuzumab Emtansine (T-DM1): An Antibody-Drug Conjugate (ADC) for HER2-Positive Breast Cancer," J Med. Chem. 57:6949-6964 (2014).
Leverson et al., "Potent and selective small-molecule MCL-1 inhibitors demonstrate on-target cancer cell killing activity as single agents and in combination with ABT-263 (navitoclax)," Cell Death and Disease 6:e1590 (2015), 11 pages.
Leverson et al., "Exploiting selective BCL-2 family inhibitors to dissect cell survival dependencies and define improved strategies for cancer therapy," Science Translational Medicine 7:279ra40, 12 pages (2015).
Lewis et al., "Differential responses of human tumor cell lines to anti-p185HER2 monoclonal antibodies," Cancer Immunol Immunother; 37:255-263 (1993).
Lindsten et al., "The Combined Functions of Proapoptotic Bcl-2 Family Members Bak and Bax Are Essential for Normal Development of Multiple Tissues," Molecular Cell 6:1389-1399 (2000).
Lonberg, "Fully human antibodies from transgenic mouse and phage display platforms," Current Opinion Immunol, 20:450-459 (2008).
Lucken-Ardjomande et al., "Newcomers in the process of mitochondrial permeabilization," J Cell Sci 118(3):473-483 (2005).
MacCallum et al., "Antibody-antigen Interactions: Contact Analysis and Binding Site Topography," J. Mol. Biol. 262:732-745 (1996).
Marty et al., "Randomized Phase II Trial of the Efficacy and Safety of Trastuzumab Combined with Docetaxel in Patients with Human Epidermal Growth Factor Receptor 2-Positive Metastatic Breast Cancer Administered as First-Line Treatment: The M77001 Study Group," J Clin Oncol 23:4265-4274 (2005).
Mikhailov et al., "Association of Bax and Bak Homo-oligomers in Mitochondria," Journal of Biological Chemistry 278(7):5367-5376 (2003).
Mikhailov et al., "Bcl-2 Prevents Bax Oligomerization in the Mitochondrial Outer Membrane," Journal of Biological Chemistry 276(21):18361-18374 (2001).
Morrison et al., "Chimeric human antibody molecules: Mouse antigen-binding domains with human constant region domains," Proc. Natl. Acad Sci. USA 81:6851-6855 (1984).
Nechushtan et al., "Bax and Bak Coalesce into Novel Mitochondria-associated Clusters during Apoptosis," Journal of Cell Biology 153(6):1265-1276 (2001).

(56) References Cited

OTHER PUBLICATIONS

Nechushtan et al., "Conformation of the Bax C-terminus regulates subcellular location and cell death," The EMBO Journal 18(9):2330-2341 (1999).
Neuberger et al., "A hapten-specific chimaeric IgE antibody with human physiological effector function," Nature 314:268-270 (1985).
Oltvai et al., "Bcl-2 Heterodimerizes In Vivo with a Conserved Homolog, Bax, That Accelerates Programed Cell Death," Cell 74:609-619 (1993).
Pegram et al., [abstract]. Proc Am Assoc Cancer Res; 38:602 (1997).
Petros et al., "Structural biology of the BcL-2 family of proteins," Biochim Biophys Acta 1644:83-94 (2004).
Petros et al., "Fragment-based discovery of potent inhibitors of the anti-apoptotic Mcl-1 protein," Bioorganic & Medicinal Chemistry Letters 24:1484-1488 (2014).
Piccart-Gebhart et al., "Trastuzumab after Adjuvant Chemotherapy in HER2-Positive Breast Cancer," N Engl. J Med 353:1659-1672 (2005).
Press et al., "Her-2/neu Expression in Node-negative Breast Cancer: Direct Tissue Quantitation by Computerized Image Analysis and Association of Overexpression with Increased Risk of Recurrent Disease," Cancer Res 53:4960-4970 (1993).
Remillard et al., "Antimitotic Activity of the Potent Tumor Inhibitor Maytansine," Science 189:1002-1005 (1975).
Riechmann et al., "Reshaping human antibodies for therapy," Nature 332:323-327 (1988).
Romond et al., "Trastuzumab plus Adjuvant Chemotherapy for Operable HER2-Positive Breast Cancer," N Engl. J Med 353:1673-1684 (2005).
Roucou et al., "Bax oligomerization in mitochondrial membranes requires tBid (caspase-8-cleaved Bid) and a mitochondrial protein," Biochemical Journal 368:915-921 (2002).
Sattler et al., "Structure of Bcl-xL-Bak Peptide Complex: Recognition Between Regulators of Apoptosis," Science 275:983-986 (1997).
Sauter et al., "Guidelines for Human Epidermal Growth Factor Receptor 2 Testing: Biologic and Methodologic Considerations," J Clin Oncol 27:1323-1333 (2009).
Schinzel et al., "Conformational control of Bax localization and apoptotic activity by Pro168," J Cell Biol 164(7):1021-1032 (2004).
Slamon et al., [abstract]. Breast Cancer Res Treat, 100 (Suppl 1):S52-S53 (2006).
Slamon et al., "Human Breast Cancer: Correlation of Relapse and Survival with Amplification of the HER-2/neu Oncogene," Science 235:177-182 (1987).
Slamon et al., "Studies of the HER-2/neu Proto-oncogene in Human Breast and Ovarian Cancer," Science 244:707-712 (1989).
Slamon et al., "Use of Chemotherapy Plus a Monoclonal Antibody Against HER2 for Metastatic Breast Cancer that Overexpresses HER2," New Engl. J. Med. 344(11):783-792 (2001).
Sleebs et al., "Discovery of Potent and Selective Benzothiazole Hydrazone Inhibitors of Bcl-XL," J. Med. Chem. 56:5514-5540 (2013).
Sliwkowski et al., "Nonclinical Studies Addressing the Mechanism of Action of Trastuzumab (Herceptin)," Seminars in Oncology 26(4), Suppl 12:60-70 (1999).
Strasser et al., "Deciphering the rules of programmed cell deathto improve therapy of cancer and other diseases," EMBO J. 30:3667-3683 (2011).
Suzuki et al., "Structure of Bax: Coregulation of Dimer Formation and Intracellular Localization," Cell 103:645-654 (2000).
Tanaka et al., "Discovery of Potent Mcl-1/Bcl-xL Dual Inhibitors by Using a Hybridization Strategy Based on Structural Analysis of Target Proteins," J. Med. Chem. 56:9635-9645 (2013).
Tao et al, "Discovery of a Potent and Selective BCL-XL Inhibitor with in Vivo Activity," ACS Med. Chem. Lett. 5:1088-1093 (2014).
Vaillant et al., "Targeting BCL-2 with the BH3 Mimetic ABT-199 in Estrogen Receptor-Positive Breast Cancer," Cancer Cell 24:120-129 (2013).
Van Dijk et al., "Human antibodies as next generation therapeutics," Curr. Opin. Chem Biol. 5:368-374 (2001).
Verma et al., "Trastuzumab Emtansine for HER2-Positive Advanced Breast Cancer," New England Journal of Medicine 367(19):1783-1791 (2012).
Vogel et al., "Efficacy and Safety of Trastuzumab as a Single Agent in First-Line Treatment of HER2-Overexpressing Metastatic Breast Cancer," J Clin Oncol 20:719-726 (2002).
Wang et al., "Mutagenesis of the BH3 Domain of BAX Identifies Residues Critical for Dimerization and Killing," Molecular and Cellular Biology 18(10):6083-6089 (1998).
Wang, "The expanding role of mitochondria in apoptosis," Genes & Development 15:2922-2933 (2001).
Wei et al., "Proapoptotic BAX and BAK: A Requisite Gateway to Mitochondrial Dysfunction and Death Science," 292(5517):727-730 (2001).
Wei et al., "tBID, a membrane-targeted death ligand, oligomerizes BAK to release cytochrome c," Genes & Development 14:2060-2071 (2000).
Winter et al., "Making Antibodies by Phage Display Technology," Ann Review Immunol, 12:433-455 (1994).
Wolter et al., "Movement of Bax from the Cytosol to Mitochondria during Apoptosis," Journal of Cell Biology 139(5):1281-1292 (1997).
Yarden et al., "Untangling the ErbB Signalling Network," Molecular Cell Biology 2:127-137 (2001).
Zha et al., "Heterodimerization-independent Functions of Cell Death Regulatory Proteins Bax and Bcl-2 in Yeast and Mammalian Cells," Journal of Biological Chemistry 272(50):31482-31488 (1997).
Zhai et al., "Comparison of chemical inhibitors of antiapoptotic Bcl-2-family proteins," Cell Death and Differentiation 13:1419-1421 (2006).
Zong et al., "Bax and Bak can localize to the endoplasmic reticulum to initiate apoptosis," Journal of Cell Biology 162:59-69 (2003).
Zong et al., "BH3-only proteins that bind pro-survival Bcl-2 family members fail to induce apoptosis in the absence of Bax and Bak," Genes and Development 15:1481-1486 (2001).
Williams et al., "Bcl-2 family proteins in breast development and cancer: could Mcl-1 targeting overcome therapeutic resistance?," Oncotarget, vol. 6, No. 6, pp. 3519-3530 (2015).
Tian Fuguo et al., "Breast Cancer: Modern Non-surgical Treatment," pp. 329-331 (Sep. 30, 2009).
English translation of Search Report dated Oct. 26, 2020 in Chinese Patent Application No. 201680040184.1 [providing a concise explanation of the Tian Fuguo et al., "Breast Cancer: Modern Non-surgical Treatment," pp. 329-331 (Sep. 30, 2009) reference].

\* cited by examiner

1 μg/mL T-DM1

| Group | H score | comments |
|---|---|---|
| Clone 7 vehicle | 15, 15, 15 | 10% of cells are 1+/2+ |
| Clone 7 T-DM1 | 30, 30 | 20% of cells are 1+/2+ |
| Clone 8 vehicle | 35, 10, 15 | 30% 1+/2+; 10% weakly 1+; 10% 1+/2+ |
| Clone 8 T-DM1 | 15, 20, 40 | 13% 1+/2+; 15% 1+/2+; 35% 1+/2+ |
| Clone 17 vehicle | 15, 10, 20 | 10% 1+/2+; 10% 1+; 15% 1+/2+ |
| Clone 17 T-DM1 | 40, 25, 25 | 30% 1+/2+; 20% 1+/2+; 20% 1+/2+ |

FIG. 7A

| Group | H score | comments |
|---|---|---|
| Clone 7 vehicle | 295, 290, 290 | 95% 3+/5% 2+; 90% 3+/10% 2+; 90% 3+/10% 2+ |
| Clone 7 T-DM1 | 290, 270 | 90% cells 3+/10% 2+; 80% 3+/10% 2+/10% 1+ |
| Clone 8 vehicle | 295, 290, 295 | 95% 3+/5% 2+; 90% 3+/10% 2+; 95% 3+/10% 2+ |
| Clone 8 T-DM1 | 295, 295, 280 | 95% 3+/5% 2+; 95% 3+/5% 2+; 85% 3+/10% 2+/5% 1+ |
| Clone 17 vehicle | 270, 235, 270 | 75% 3+/20% 2+/5% 1+; 35% 3+/65% 2+; 75% 3+/20% 2+/5% 1+ |
| Clone 17 T-DM1 | 275, 260, 290 | 75% 3+/25% 2+; 70% 3+/20% 2+/10% 1+; 90% 3+/10% 2+ |

FIG. 7B

```
1                                          15                     30                  45
DIQMTQSPSSLSASVGDRVTITCRASQDVNTAVAWYQQKPGKAPK 46                                         60                    75                   90
LLIYSASFLYSGVPSRFSGSRSGTDFTLTISSLQPEDFATYYCQQ 91                                        105                   120                  135
HYTTPPTFGQGTKVEIKRTVAAPSVFIFPPSDEQLKSGTASVVCL 136                                       150                   165                  180
LNNFYPREAKVQWKVDNALQSGNSQESVTEQDSKDSTYSLSSTLT 181                                       195                   210        214
LSKADYEKHKVYACEVTHQGLSSPVTKSFNRGEC
```

FIG. 13

```
  1 EVQLVESGGG LVQPGGSLRL SCAASGFNIK DTYIHWVRQA PGKGL 45
 46 EWVARIYPTN GYTRYADSVK GRFTISADTS KNTAYLQMNS LRAED 90
 91 TAVYYCSRWG GDGFYAMDYW GQGTLVTVSS ASTKGPSVFP LAPSS 135
136 KSTSGGTAAL GCLVKDYFPE PVTVSWNSGA LTSGVHTFPA VLQSS 180
181 GLYSLSSVVT VPSSSLGTQT YICNVNHKPS NTKVDKKVEP KSCDK 225
226 THTCPPCPAP ELLGGPSVFL FPPKPKDTLM ISRTPEVTCV VVDVS 270
271 HEDPEVKFNW YVDGVEVHNA KTKPREEQYN STYRVVSVLT VLHQD 315
316 WLNGKEYKCK VSNKALPAPI EKTISKAKGQ PREPQVYTLP PSREE 360
361 MTKNQVSLTC LVKGFYPSDI AVEWESNGQP ENNYKTTPPV LDSDG 405
406 SFFLYSKLTV DKSRWQQGNV FSCSVMHEAL HNHYTQKSLS LSPG  449
```

FIG. 14

COMBINATION THERAPY WITH AN ANTI-HER2 ANTIBODY-DRUG CONJUGATE AND A BCL-2 INHIBITOR

CROSS-REFERENCE TO RELATED APPLICATIONS

This application is a continuation of PCT Application No. PCT/US2016/041184, filed Jul. 6, 2016, which claims benefit of priority under 35 USC § 119(e) of U.S. Provisional Application No. 62/189,610, filed Jul. 7, 2015, the full disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jun. 28, 2016, is named GNE-0416-WO.txt and is 6,298 bytes in size.

TECHNICAL FIELD

The present invention is directed to a combination therapy involving an anti-HER2 antibody-drug conjugate and a Bcl-2 inhibitor for the treatment of cancer. In a particular embodiment, the invention concerns methods of using trastuzumab-MCC-DM1 (trastuzumab emtansine; KADCYLA®) and a selective Bcl-2 inhibitor for the treatment of HER2-positive cancer, such as HER2-positive breast cancer or gastric cancer.

BACKGROUND

Anti-HER2 Antibody-Drug Conjugates

The HER2 (ErbB2) receptor tyrosine kinase is a member of the epidermal growth factor receptor (EGFR) family of transmembrane receptors. Overexpression of HER2 is observed in approximately 20% of human breast cancers (hereinafter referred to as HER2-positive breast cancer) and is implicated in the aggressive growth and poor clinical outcomes associated with these tumors (Slamon et al (1987) Science 235:177-182). HER2 protein overexpression can be determined using an immunohistochemistry based assessment of fixed tumor blocks (Press M F, et al (1993) Cancer Res 53:4960-70).

Trastuzumab (CAS 180288-69-1, HERCEPTIN®, huMAb4D5-8, rhuMAb HER2, Genentech) is a recombinant DNA-derived, IgG1 kappa, monoclonal antibody that is a humanized version of a murine anti-HER2 antibody (4D5) that selectively binds with high affinity in a cell-based assay (Kd=5 nM) to the extracellular domain of HER2 (U.S. Pat. Nos. 5,677,171; 5,821,337; 6,054,297; 6,165,464; 6,339,142; 6,407,213; 6,639,055; 6,719,971; 6,800,738; 7,074,404; Coussens et al (1985) Science 230:1132-9; Slamon et al (1989) Science 244:707-12; Slamon et al (2001) New Engl. J. Med. 344:783-792). Trastuzumab has been shown, in both in vitro assays and in animals, to inhibit the proliferation of human tumor cells that overexpress HER2 (Hudziak et al (1989) Mol Cell Biol 9:1165-72; Lewis et al (1993) Cancer Immunol Immunother; 37:255-63; Baselga et al (1998) Cancer Res. 58:2825-2831). Trastuzumab is a mediator of antibody-dependent cellular cytotoxicity, ADCC (Lewis et al (1993) Cancer Immunol Immunother 37(4): 255-263; Hotaling et al (1996) [abstract]. Proc. Annual Meeting Am Assoc Cancer Res; 37:471; Pegram M D, et al (1997) [abstract]. Proc Am Assoc Cancer Res; 38:602; Sliwkowski et al (1999) Seminars in Oncology 26(4), Suppl 12:60-70; Yarden Y. and Sliwkowski, M. (2001) Nature Reviews: Molecular Cell Biology, Macmillan Magazines, Ltd., Vol. 2:127-137).

HERCEPTIN® was approved in 1998 for the treatment of patients with HER2-overexpressing metastatic breast cancers (Baselga et al, (1996) J. Clin. Oncol. 14:737-744) that have received extensive prior anti-cancer therapy, and has since been used in over 300,000 patients (Slamon D J, et al. N Engl J Med 2001; 344:783-92; Vogel C L, et al. J Clin Oncol 2002; 20:719-26; Marty M, et al. J Clin Oncol 2005; 23:4265-74; Romond E H, et al. T N Engl J Med 2005; 353:1673-84; Piccart-Gebhart M J, et al. N Engl J Med 2005; 353:1659-72; Slamon D, et al. [abstract]. Breast Cancer Res Treat 2006, 100 (Suppl 1): 52). In 2006, the FDA approved HERCEPTIN® (trastuzumab, Genentech Inc.) as part of a treatment regimen containing doxorubicin, cyclophosphamide and paclitaxel for the adjuvant treatment of patients with HER2-positive, node-positive breast cancer.

An alternative approach to antibody-targeted therapy is to utilize antibodies for delivery of cytotoxic drugs specifically to antigen-expressing cancer cells. Antibody-drug conjugates, or ADCs, are monoclonal antibodies to which highly potent cytotoxic agents have been conjugated. ADCs represent a novel approach to conferring tumor selectivity on systemically administered anti-tumor therapeutics. Utilizing surface antigens that are tumor-specific and/or overexpressed, ADCs are designed to focus the delivery of highly potent cytotoxic agents to tumor cells. The potential of this approach is to create a more favorable therapeutic window for such agents than could be achieved by their administration as free drugs.

Maytansinoids, derivatives of the anti-mitotic drug maytansine, bind to microtubules in a manner similar to *vinca* alkaloid drugs (Issell B F et al (1978) Cancer Treat. Rev. 5:199-207; Cabanillas F et al. (1979) Cancer Treat Rep, 63:507-9. DM1 is a thiol-containing maytansinoid derived from the naturally occurring ester ansamitocin P3 (Remillard S, Rebhun L I, Howie G A, et al. (1975) Science 189(4207): 1002-1005.3; Cassady J M, Chan K K, Floss H G. (2004) Chem Pharm Bull 52(1): 1-26.4). The related plant ester, maytansine, has been studied as a chemotherapeutic agent in approximately 800 patients, administered at a dose of 2.0 mg/m2 every 3 weeks either as a single dose or for 3 consecutive days (Issell B F, Crooke S T. (1978) Maytansine. Cancer Treat Rev 5:199-207). Despite preclinical activity, the activity of maytansine in the clinic was modest at doses that could be safely delivered. The dose-limiting toxicity (DLT) was gastrointestinal, consisting of nausea, vomiting, and diarrhea (often followed by constipation). These toxicities were dose dependent but not schedule dependent. Peripheral neuropathy (predominantly sensory) was reported and was most apparent in patients with preexisting neuropathy. Subclinical transient elevations of hepatic transaminase, alkaline phosphatase, and total bilirubin were reported. Constitutional toxicities, including weakness, lethargy, dysphoria, and insomnia, were common. Less common toxicities included infusion-site phlebitis and mild myelosuppression. Further development of the drug was abandoned in the 1980s because of the narrow therapeutic window.

Trastuzumab-MCC-DM1 (T-DM1, trastuzumab emtansine, ado-trastuzumab emtansine, KADCYLA®), a novel antibody-drug conjugate (ADC) for the treatment of HER2-positive breast cancer, is composed of the cytotoxic agent DM1 (a thiol-containing maytansinoid anti-microtubule agent) conjugated to trastuzumab at lysine side chains via an MCC linker, with an average drug load (drug to antibody ratio) of 3.5. After binding to HER2 expressed on tumor cells, T-DM1 undergoes receptor-mediated internalization, resulting in intracellular release of cytotoxic DM1-containing catabolites and subsequent cell death.

In a Phase I study of T-DM1 (TDM3569g), the maximum tolerated dose (MTD) of T-DM1 administered by IV infusion every 3 weeks (q3w) was 3.6 mg/kg. A DLT (Dose-Limiting Toxicity) consisted of transient thrombocytopenia in patients treated at 4.8 mg/kg. Treatment with 3.6 mg/kg q3w was well tolerated and associated with significant clinical activity. (Krop (2010) J. Clin. Oncol. 28(16):2698-2704). That same study also showed that weekly dosing with 2.4 mg/kg was also well tolerated and had anti-tumor activity. (Beeram (2012) Cancer 118(23):5733-5740.)

A Phase II study (TDM4374g) demonstrated that T-DM1, administered at 3.6 mg/kg q3w, had single-agent anti-tumor activity in a heavily pre-treated patient population having HER2-positive metastatic breast cancer. (Krop (2012) 30(26):3234-3241.) A Phase III study (TDM4370g) demonstrated that T-DM1, administered at 3.6 mg/kg q3w, significantly prolonged progression-free survival and overall survival with less toxicity compared to treatment with lapatinib plus capecitabine in patients with HER2-positive advanced breast cancer previously treated with trastuzumab and a taxane. (Verma (2012) New England Journal of Medicine 367:1783-1791.)

The U.S. Food and Drug Administration approved ado-trastuzumab emtansine, marketed under the tradename KADCYLA®, on Feb. 22, 2013 for the treatment of patients with HER2-positive, metastatic breast cancer who previously received treatment with trastuzumab and a taxane.

Bcl-2 Inhibitors

The Bcl-2 family of proteins regulates programmed cell death triggered by developmental cues and in response to multiple stress signals (Cory. S., and Adams, J. M., Nature Reviews Cancer 2 (2002) 647-656; Adams, Genes und Development 17 (2003) 2481-2495; Danial, N. N., and Korsmeyer, S. J., Cell 116 (2004) 205-219). Whereas cell survival is promoted by Bcl-2 itself and several close relatives (Bcl-xL, Bcl-W, Mcl-1 and Al), which bear three or four conserved Bcl-2 homology (BH) regions, apoptosis is driven by two other sub-families. The initial signal for cell death is conveyed by the diverse group of BH3-only proteins, including Bad, Bid, Bim, Puma and Noxa, which have in common only the small BH3 interaction domain (Huang and Strasser, Ce 11103 (2000) 839-842). However, Bax or Bak, multi-domain proteins containing BH1-BH3, are required for commitment to cell death (Cheng, et al., Molecular Cell 8 (2001) 705-711; Wei, M. C., et al., Science 292 (2001) 727-730; Zong, W. X., et al., Genes and Development 15 148 (2001) 1-1486). When activated, they can permeabilize the outer membrane of mitochondria and release pro-apoptogenic factors (e.g. cytochrome C) needed to activate the caspases that dismantle the cell (Wang, K., Genes and Development 15 (2001) 2922-2933; (Adams, 2003 supra); Green, D. R., and Kroemer, G., Science 305 (2004) 626-629).

Interactions between members of these three factions of the Bcl-2 family dictate whether a cell lives or dies. When BH3-only proteins have been activated, for example, in response to DNA damage, they can bind via their BH3 domain to a groove on their pro-survival relatives (Sattler, et al., Science 275 (1997) 983-986). How the BH3-only and Bcl-2-like proteins control the activation of Bax and Bak, however, remains poorly understood (Adams, 2003 supra).

Most attention has focused on Bax. This soluble monomeric protein (Hsu, Y. T., et al., Journal of Biological Chemistry 272 (1997) 13289-1 3834; Wolter, K. G., et al., Journal of Cell Biology 139 (1997) 1281-92) normally has its membrane targeting domain inserted into its groove, probably accounting for its cytosolic localization (Nechushtan, A., et al., EMBO Journal 18 (1999) 2330-2341; Suzuki, et al., Cell 103 (2000) 645-654; Schinzel, A., et al., J Cell Biol 164 (2004) 1021-1032). Several unrelated peptides/proteins have been proposed to modulate Bax activity, reviewed in Lucken-Ardjomande, S., and Martinou, J. C., J Cell Sci 118 (2005) 473-483, but their physiological relevance remains to be established. Alternatively, Bax may be activated via direct engagement by certain BH3-only proteins (Lucken-Ardjomande, S., and Martinou, J. C, 2005 supra), the best documented being a truncated form of Bid, tBid (Wei, M. C., et al., Genes und Development 14 (2000) 2060-2071; Kuwana, T., et al., Cell 111 (2002) 331-342; Roucou, X., et al., Biochemical Journal 368 (2002) 915-921; Cartron, P. F., et al., Mol Cell 16 (2004) 807-818). As discussed elsewhere (Adams 2003 supra), the oldest model, in which Bcl-2 directly engages Bax (Oltvai, Z. N., et al., Cell 74 (1993) 609-619), has become problematic because Bcl-2 is membrane bound while Bax is cytosolic, and their interaction seems highly dependent on the detergents used for cell lysis (Hsu, Y. T., and Youle, 1997 supra). Nevertheless, it is well established that the BH3 region of Bax can mediate association with Bcl-2 (Zha, H., and Reed, J., Journal of Biological Chemistry 272 (1997) 31482-88; Wang, K., et al., Molecular und Cellular Biology 18 (1998) 6083-6089) and that Bcl-2 prevents the oligomerization of Bax, even though no heterodimers can be detected (Mikhailov, V., et al., Journal of Biological Chemistry 276 (2001) 18361-18374). Thus, whether the pro-survival proteins restrain Bax activation directly or indirectly remains uncertain.

Although Bax and Bak seem in most circumstances to be functionally equivalent (Lindsten, T., et al., Molecular Cell 6 (2000) 1389-1399; Wei, M. C., et al., 2001 supra), substantial differences in their regulation would be expected from their distinct localization in healthy cells. Unlike Bax, which is largely cytosolic, Bak resides in complexes on the outer membrane of mitochondria and on the endoplasmic reticulum of healthy cells (Wei, M. C., et al., 2000 supra; Zong, W. X., et al., Journal of Cell Biology 162 (2003) 59-69). Nevertheless, on receipt of cytotoxic signals, both Bax and Bak change conformation, and Bax translocates to the organellar membranes, where both Bax and Bak then form homo-oligomers that can associate, leading to membrane permeabilization (Hsu, Y. T., et al., PNAS 94 (1997) 3668-3672; Wolter, K. G., et al., 1997 supra; Antonsson, B., et al., Journal of Biological Chemistry 276 (2001) 11615-11623; Nechushtan, A., et al., Journal of Cell Biology 153 (2001) 1265-1276; Wei, M. C., et al., 2001 supra; Mikhailov, V., et al., Journal of Biological Chemistry 278 (2003) 5367-5376).

There exist various Bcl-2 inhibitors, which all have the same property of inhibiting prosurvival members of the Bcl-2 family of proteins and are therefore promising candidates for the treatment of cancer. Such Bcl-2 inhibitors are e.g. Oblimersen, SPC-2996, RTA-402, Gossypol, AT-101, Obatoclax mesylate, A-371191, A-385358, A-438744, ABT-737, ABT-263 (navitoclax), AT-101, BL-11, BL-193, GX-15-003, 2-Methoxyantimycin $A_3$, HA-14-1, KF-67544, Purpurogallin, TP-TW-37, YC-137 and Z-24, and are described e.g. in Zhai, D., et al., Cell Death and Differentiation 13 (2006) 1419-1421.

The link between other the Bcl-2 family proteins and cancer is also well established and amply documented (Strasser, A. 2011 *EMBO J.* 30, 3667-3683), and inhibitors of other Bcl family members are also known. Bcl-$X_L$-selective inhibitors A-1155463 and A-1331852 are described, for example, in Leverson et al., *Science Translational Medicine* Vol 7, Issue 279 279ra40. Selective benzothiazole hydrazone inhibitors of Bcl-$X_L$ are disclosed in Sleebs et al., *J. Med. Chem.* 2013, 56, 5514-5540. For the description of other Bcl-$X_L$ inhibitors see, e.g. Koehler et al., *ACSMed. Chem. Lett.* 2014, 5, 662-667; and Tao et al, *ACSMed. Chem. Lett.* 2014, 5, 1088-10. MCl-1 inhibitors and their uses as cancer therapeutics are described, for example, in Leverson et al., *Cell Death and Disease* (2015) 6, e1590; Bruncko et al., *J. Med. Chem.* 2015, 58, 2180-2194; Petros et al., *Bioorganic & Medicinal Chemistry Letters* 24 (2014) 1484-1488; Abulwerdi et al., *Mol Cancer Ther* 2014; 13:565-5; Abulwerdi et al., *J. Med. Chem.* 2014, 57, 4111-4133; Burke et al., *J. Med. Chem.* 2015, 58, 3794-3805; Friberg et al., *J. Med. Chem.* 2013, 56, 15-30; and belmar et al., *Pharmacology & Therapeutics* 145 (2015) 76-84. Mcl-1/Bcl-xL dual inhibitors are disclosed by Tanaka et al., *J. Med. Chem.* 2013, 56, 9635-9645.

SUMMARY OF THE INVENTION

In one aspect, the invention concerns a method for the treatment of a cancer in a human in need thereof comprising administering to such human an effective amount of an anti-HER2 antibody-drug conjugate and an inhibitor of a Bcl family protein.

In another aspect, the invention concerns a method for the treatment of a cancer in a human in need thereof comprising administering to such human an effective amount of an anti-HER2 antibody-drug conjugate and a selective Bcl-2 inhibitor.

In one embodiment, the cancer is HER2 positive cancer.

In another embodiment, the cancer is HER2 positive breast cancer or gastric cancer.

In yet another embodiment, the HER2-positive breast cancer or gastric cancer has a HER2 immunohistochemistry (IHC) score of 2+ or 3+ and/or an in situ hybridization (ISH) amplification ratio (her2: CEP17 in situ hybridization (ISH) amplification ratio) of ≥2.0.

In a further embodiment, the HER2-positive cancer, such as breast cancer or gastric cancer, is resistant to treatment with an anti-HER2 antibody-drug conjugate administered as a single agent.

In a still further embodiment, the HER2-positive cancer, such as breast cancer or gastric cancer, is sensitive to treatment with an anti-HER2 antibody-drug conjugate administered as a single agent, and the combination of the anti-HER2 antibody-drug conjugate and the selective Bcl-2 inhibitor can be administered to a patient naïve to treatment with the anti-HER2 antibody-drug conjugate.

In a different embodiment, the anti-HER2 antibody-drug conjugate and the selective Bcl-2 inhibitor show synergistic activity, including, but not limited to, synergistic activity in a HER2-positive cancer, such as breast cancer or gastric cancer, that is resistant to treatment with an anti-HER2 antibody-drug conjugate administered as a single agent.

In all embodiments, the anti-HER2 antibody-drug conjugate can, for example, be trastuzumab-MCC-DM1.

In all embodiments, the selective Bcl-2 inhibitor can, for example, be 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof.

In another aspect, the invention concerns a method for the treatment of HER2 positive cancer in a human in need thereof comprising administering to the human an effective amount of trastuzumab-MCC-DM 1 and 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof.

In one embodiment, the cancer is HER2 positive breast cancer or gastric cancer.

In another embodiment, the HER2-positive breast cancer or gastric cancer has a HER2 immunohistochemistry (IHC) score of 2+ or 3+ and/or an in situ hybridization (ISH) amplification ratio (her2: CEP17 in situ hybridization (ISH) amplification ratio) of ≥2.0.

In yet another embodiment, the HER2 positive cancer, such as breast cancer or gastric cancer, is resistant to treatment with trastuzumab-MCC-DM1 administered as a single agent.

In a further embodiment, the HER2-positive cancer, such as breast cancer or gastric cancer, is sensitive to treatment with trastuzumab-MCC-DM1 administered as a single agent, and the combination of the trastuzumab-MCC-DM1 and 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof can be administered to a patient naïve to treatment with trastuzumab-MCC-DM1.

In a still further embodiment, the HER2-positive cancer, such as breast cancer or gastric cancer, is sensitive to treatment with an anti-HER2 antibody-drug conjugate administered as a single agent, and the combination of the anti-HER2 antibody-drug conjugate and the selective Bcl-2 inhibitor can be administered to a patient naïve to treatment with the anti-HER2 antibody-drug conjugate. In a further embodiment, the trastuzumab-MCC-DM1 and the 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof show synergistic activity, including, but not limited to, synergistic activity in a HER2-positive cancer, such as breast cancer or gastric cancer.

In a still further embodiment, the trastuzumab-MCC-DM1 and the 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof are co-administered.

In another embodiment, the trastuzumab-MCC-DM1 and the 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof are administered simultaneously.

In yet another embodiment, the trastuzumab-MCC-DM1 and the 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof are administered consecutively.

In another aspect, the invention concerns the use of a combination of an anti-HER2 antibody-drug conjugate and an inhibitor of a Bcl family protein in the preparation of a medicament for the treatment of cancer.

In one embodiment, the Bcl family protein is a Bcl-2 like protein, such as Mcl-1, Bcl-xl, Bcl-w (BCL2L2), or Bcl-xs, preferably Mcl-1 or Bcl-xl.

In another aspect, the invention concerns the use of a combination of an anti-HER2 antibody-drug conjugate and a selective Bcl-2 inhibitor in the preparation of a medicament for the treatment of cancer.

In one embodiment, the invention concerns the use of a combination of trastuzumab-MCC-DM1 and 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof in the preparation of a medicament for the treatment of cancer.

In all embodiments, the cancer may be HER2 positive cancer.

In all embodiments, the cancer may, for example, be breast cancer or gastric cancer.

In all embodiments, the HER2 positive cancer, such as breast cancer or gastric cancer, may be resistant to treatment with trastuzumab-MCC-DM1 administered as a single agent.

In all embodiments, the HER2-positive cancer, such as breast cancer or gastric cancer, may be sensitive to treatment with trastuzumab-MCC-DM1 administered as a single agent, and the combination of the trastuzumab-MCC-DM1 and 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof may be used to treat a patient naïve to treatment with trastuzumab-MCC-DM1.

In another aspect, the invention concerns the use of a combination of an anti-HER2 antibody-drug conjugate and an inhibitor of a Bcl family protein in the preparation of a medicament for the treatment of cancer.

In one embodiment, the Bcl family protein is a Bcl-2 like protein, such as Mcl-1, Bcl-xl, Bcl-w (BCL2L2), or Bcl-xs, preferably Mcl-1 or Bcl-xl.

In a further aspect, the invention concerns a combination of an anti-HER2 antibody-drug conjugate and a selective Bcl-2 inhibitor for use in the treatment of cancer.

In one embodiment, the combination of trastuzumab-MCC-DM1 and 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof is for use in the treatment of cancer.

In all combinations, the cancer may, for example, be HER2 positive cancer, such as HER2 positive breast cancer or gastric cancer.

In a particular embodiment, the cancer, such as breast cancer or gastric cancer, is resistant to treatment with the anti-HER2 antibody-drug conjugate or the trastuzumab-MCC-DM1, when administered as a single agent.

In another embodiment, the HER2-positive cancer, such as breast cancer or gastric cancer, may be sensitive to treatment with the anti-HER2 antibody-drug conjugate, e.g. trastuzumab-MCC-DM1, when administered as a single agent, and the combination may be used to treat a patient naïve to treatment the anti-HER2 antibody-drug conjugate, e.g. trastuzumab-MCC-DM1.

In another aspect, the invention concerns a method for the diagnosis of a HER2-positive tumor resistant to treatment with an anti-HER2 antibody-drug conjugate, comprising determining in a tumor sample obtained from a patient with HER2-positive cancer the expression level of the Bcl-2 gene or its product relative to the expression level in a control sample, and diagnosing said cancer as resistant to treatment with said anti-HER2 antibody-drug conjugate when the expression level in said tumor sample is at least 2 fold, or at least 3 fold or at least 4 fold, or at least 5 fold greater than the expression level in said control sample.

In a further aspect, the invention concerns a method for the diagnosis of a HER2-positive tumor susceptible to treatment with an anti-HER2 antibody-drug conjugate, comprising determining in a tumor sample obtained from a patient with HER2-positive cancer the expression level of the Bcl-2 gene or its product relative to the expression level in a control sample, and diagnosing said cancer as susceptible to treatment with said anti-HER2 antibody-drug conjugate when the expression level in said tumor sample is less than 2 fold, or at least 3 fold, or at least 4 fold, or at least 5 fold greater than the expression level in said control sample.

In a still further aspect, the invention concerns a method for the diagnosis of a subject with a HER2-positive tumor as being resistant or susceptible to treatment with an anti-HER2 antibody-drug conjugate, comprising (i) obtaining a tumor sample from said subject, (ii) measuring the expression level of the Bcl-2 gene or its product in said tumor sample relative to a control sample, and (iii) diagnosing said tumor as being resistant to treatment with an anti-HER2 antibody-drug conjugate when the measured expression level of Bcl-2 in said tumor sample is at least 2 fold, or at least 3 fold, or at least 4 fold, or at least 5 fold greater than the expression level in said control sample, or diagnosing said tumor as being susceptible to treatment with an anti-HER2 antibody-drug conjugate when the measured expression level of Bcl-2 in said tumor sample is less than 2 fold, or less than 3 fold, or less than 4 fold, or less than 5 fold greater than the expression level in said control sample.

In one embodiment, the subject is a human patient.

In another embodiment, the control sample is a tumor sample of the same cell type that is not resistant to treatment with said anti-HER2 antibody-drug conjugate.

In yet another embodiment, the tumor is breast cancer or gastric cancer.

In a further embodiment, the tumor sample is a formalin-fixed, paraffin-embedded tumor sample.

In all embodiments, the diagnostic method may further comprise a step of measuring the expression level of the HER2 gene or its product in the tumor sample.

In all embodiments, the diagnostic method may further comprise a step of treating the subject with an anti-HER2 antibody-drug conjugate and a selective Bcl-2 inhibitor when the measured expression level of Bcl-2 in the tumor sample is at least 2 fold, or at least 3 fold, or at least 4 fold, or at least 4 fold, or at least 5 fold greater than the expression level in said control sample.

In all embodiments, the diagnostic method may further comprise a step of treating said patient with an anti-HER2 antibody-drug conjugate when the measured expression level of Bcl-2 in the tumor sample is less than 2-times greater than the expression level in said control sample.

In one embodiment, the anti-HER2 antibody-drug conjugate is trastuzumab-MCC-DM1.

In another embodiment, the selective Bcl-2 inhibitor 2-(1H-pyrrolo[2,3-b]pyridin-5-yloxy)-4-(4-((2-(4-chlorophenyl)-4,4-dimethylcyclohex-1-enyl)methyl)piperazin-1- yl)-N-(3-nitro-4-((tetrahydro-2H-pyran-4-yl)methylamino)
phenylsulfonyl)benzamide or a pharmaceutically acceptable
salt thereof.

In another aspect, the invention concerns a kit for the in vitro diagnosis or prognosis of a HER2 positive tumor resistant to treatment with an anti-HER2 antibody-drug conjugate in a biological sample obtained from a patient, which comprises a specific binding partner for the Bcl-2 gene or its expression product.

In one embodiment, the binding partner is an anti-Bcl-2 antibody.

In another embodiment, the binding partner is a nucleic acid hybridizing to the Bcl-2 gene.

In a further aspect, the invention relates to a kit comprising an anti-HER2 antibody drug conjugate and a selective Bcl-2 inhibitor for the combination treatment of a patient with a HER2 expressing cancer.

In an embodiment of the present invention, the kit further comprises a pharmaceutically acceptable carrier. The kit may further include a sterile diluent, which is preferably stored in a separate additional container. The kit may further include a package insert comprising printed instructions directing the use of the combined treatment as a method for a HER2 expressing cancer, such as HER2 expressing breast or gastric cancer.

Just as in other aspects, the HER2 expressing cancer may, for example, be breast cancer or gastric cancer, and in various embodiments the anti-HER2 antibody drug conjugate may be trastuzumab-MCC-DM1 and/or the selective Bcl-2 inhibitor may be 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof.

In a particular embodiment, the HER2 expressing cancer to be treated, such as breast cancer or gastric cancer, is resistant to treatment with the anti-HER2 antibody-drug conjugate or the trastuzumab-MCC-DM1, when administered as a single agent.

In another embodiment, the HER2 expressing cancer, such as breast cancer or gastric cancer, may be sensitive to treatment with the anti-HER2 antibody-drug conjugate, e.g. trastuzumab-MCC-DM1, when administered as a single agent, and the combination may be used to treat a patient naïve to treatment the anti-HER2 antibody-drug conjugate, e.g. trastuzumab-MCC-DM1.

BRIEF DESCRIPTION OF THE FIGURES

FIG. 1A shows mRNA expression assessed by TaqMan qRT-PCR analysis; FIG. 1B shows protein expression by Western blot analysis.

FIG. 7A shows the expression of Bcl-2 in formalin-fixed paraffin-embedded T-DM1 resistant KPL-4 xenograft tumor samples (Clones #8 and #17) determined by immunohistochemistry (IHC), using DAB detection method.

FIG. 7B shows the expression of HER2 (ErbB2) in formalin-fixed paraffin-embedded T-DM1 resistant KPL-4 xenograft tumor samples (Clones #8 and #17) determined by immunohistochemistry (IHC), using DAB detection method.

The results demonstrate no induction of apoptosis by T-DM1 alone but enhanced apoptosis with all combinations tested.

Figure 10A:
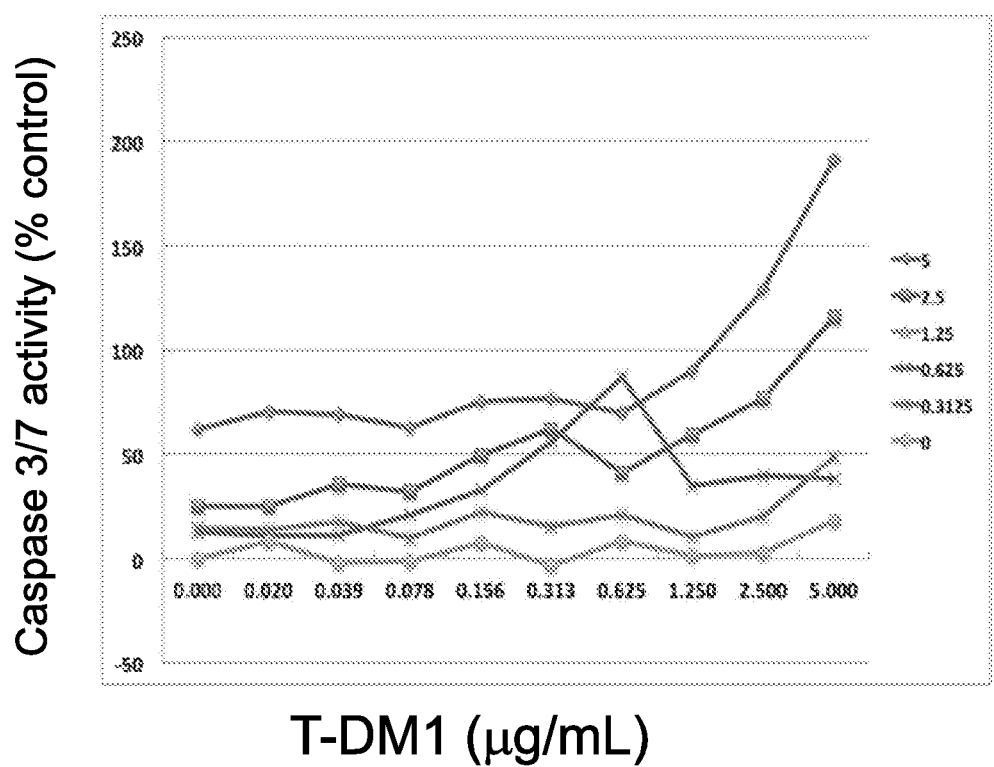
FIG. 10A presents the results of a caspase 3/7 activation luminescent in vitro apoptosis assay, testing the effect of five separate concentrations of GDC-0199 (µM) in combination with 9 different concentrations for 24 hours of treatment in HER2+ HCC1569 breast cancer cells (T-DM1 naive cells).
Figure 10B:
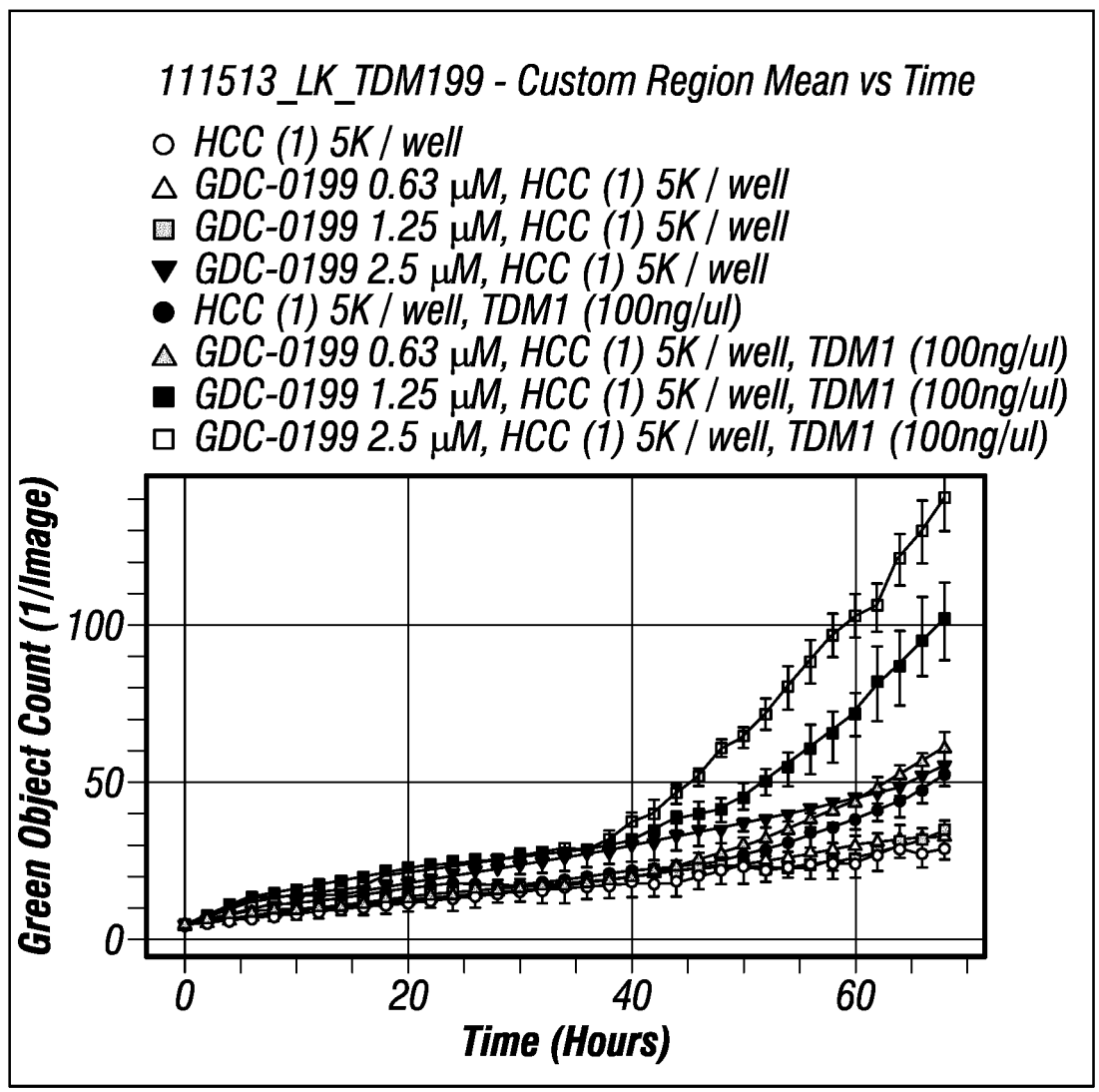

FIG. 10B presents the results of a kinetic caspase 3/7 fluorescent in vitro apoptosis assay, testing the effect of three different concentrations of GDC-0199 (0.63 µM, 1.25 µM, 2.5 µM), alone and in combination with T-DM1 (0.1 µg/mL), in HER2+ HCC1569 breast cancer cells. The results demonstrate dose-dependent enhanced caspase activation with combination treatment.

Figure 11:
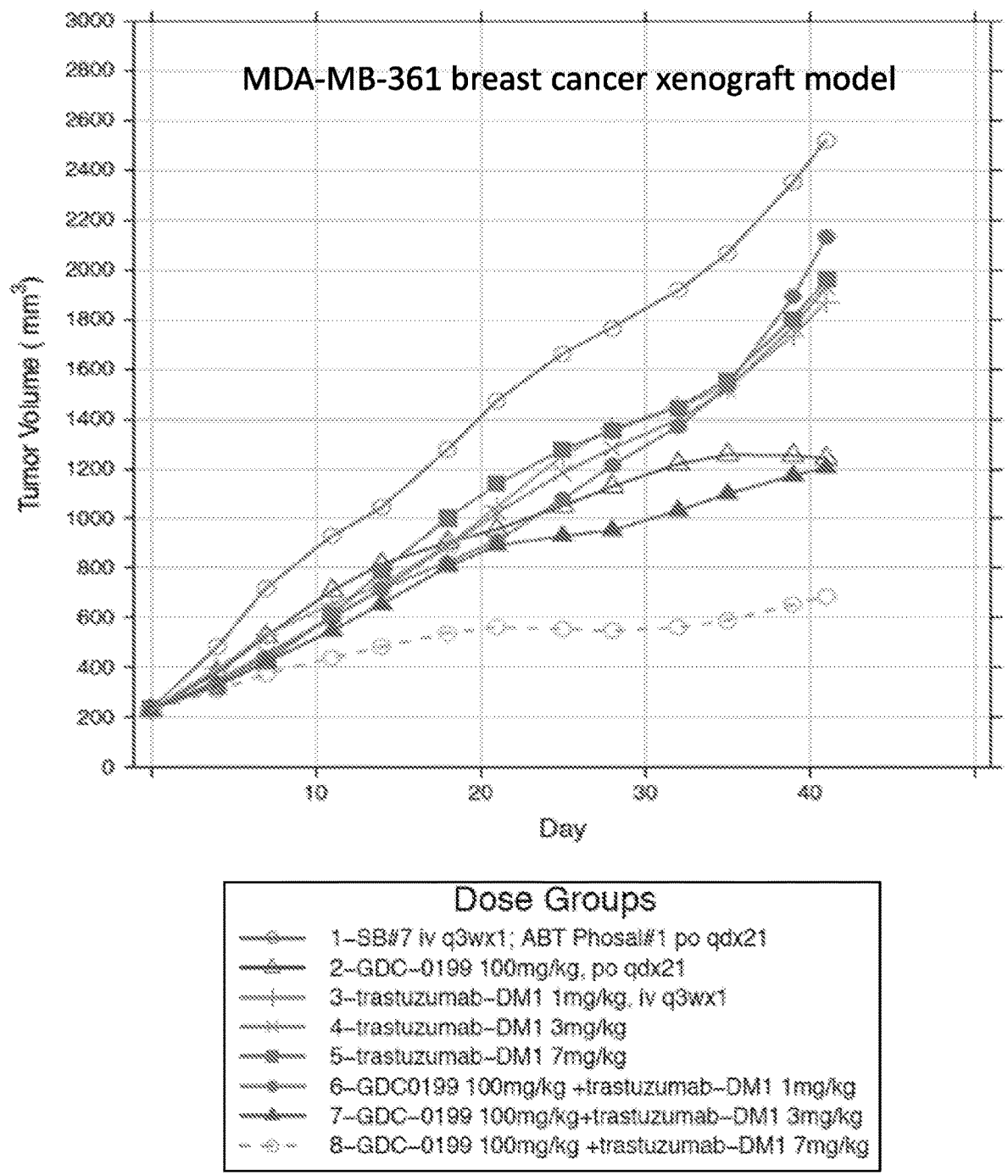

FIG. 11 shows the effect of T-DM1 (1 mg/kg, 3 mg/kg, 7 mg/kg, iv q3wxl) and GDC-0199 (100 mg/kg, po, qd×21), alone or in combination, on tumor growth in HER2+ MDA-MB-361 breast cancer xenograft model. Significant tumor growth delay was observed with GDC-0199 combined with 7 mg/kg T-DM1.

Figure 12:
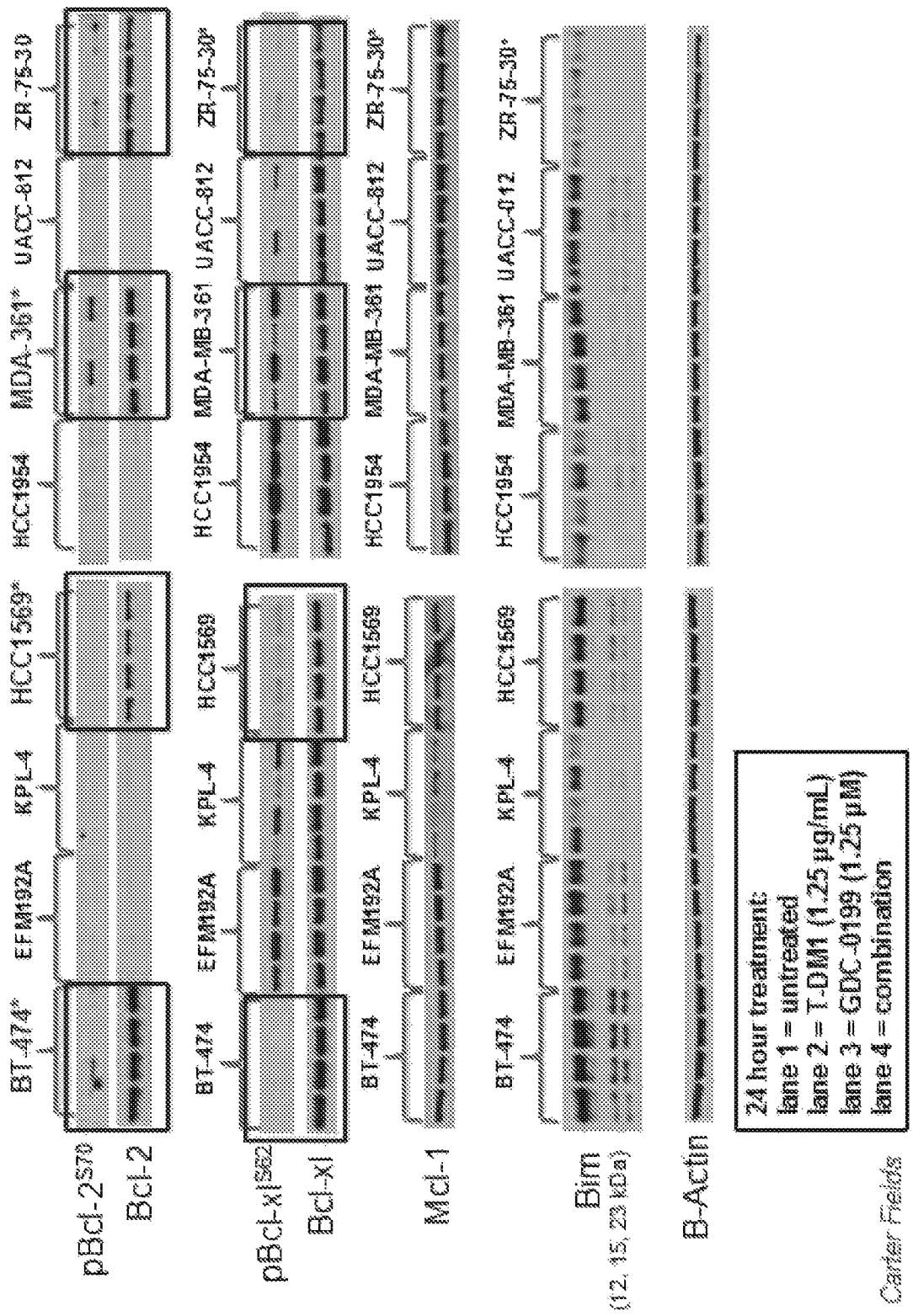

FIG. 12 shows Western blot analysis of the effects of T-DM1, with or without GDC-0199, on Bcl-2 family members (total and phospho-Bcl-2 and -Bcl-xL, total Mcl-1 and Bim) in HER2+ breast cancer cell lines BT-474, EFM192A, KPL-4, HCC1569, HCC1954, MDA-361, UACC-812, ZR-75-30.

FIG. 13 shows the amino acid sequence of trastuzumab light chain (SEQ ID NO: 1).

FIG. 14 shows the amino acid sequence of trastuzumab heavy chain (SEQ ID NO: 2).

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described.

All references cited throughout the disclosure are expressly incorporated by reference herein in their entirety. In the event that one or more of the incorporated literature, patents, and similar materials differs from or contradicts this application, including but not limited to defined terms, term usage, described techniques, or the like, this application controls.

Definitions

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The anti-HER2 antibody used in the antibody-drug conjugates herein is a monoclonal antibody.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are especially preferred. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric and bifunctional antibodies.

The term "human antibody", as used herein, is intended to include antibodies having variable and constant regions derived from human germline immunoglobulin sequences. Human antibodies are well-known in the state of the art (van Dijk, M. A., and van de Winkel, J. G., Curr. Opin. Pharmacol. 5 (2001) 368-374) and can be produced by a variety of teachniques, including phage display. Based on such technology, human antibodies against a great variety of targets can be produced. Examples of human antibodies are for example described in Kellermann, S. A., et al., Curr Opin Biotechnol. 13 (2002) 593-597. For the use of phage display technology to produce and select human antibodies see, e.g., Winter et al., Ann Review Immunol, 1994, 12:433-455; and for the production of fully human antibodies from transgenic mouse and phage display platforms see, e.g., Lonberg, Current Opinion Immunol, 2008, 20(4):450-459.

The term "recombinant human antibody", as used herein, is intended to include all human antibodies that are prepared, expressed, created or isolated by recombinant means, such as, for example, antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form.

As used herein, "specifically binding" or "binds specifically to" refers a binding that is sufficiently selective to a target as to distinguish it from a binding to unwanted or nonspecific targets. In one embodiment, an antibody that binds specifically to a target will have a binding affinity for that target (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In yet another embodiment, the KD is $10^{-10}$ mol/l or lower (e.g. $10^{-12}$ mol/l). The binding affinity is determined with a standard binding assay, such as Scatchard plot analysis on cells expressing the target antigen.

The term "nucleic acid molecule", as used herein, is intended to include DNA molecules and RNA molecules. A nucleic acid molecule may be single-stranded or double-stranded. In one embodiment, it is double-stranded DNA.

The "constant domains" are not involved directly in binding the antibody to an antigen but are involved in the effector functions (ADCC, complement binding, and CDC).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6*th* ed., W.H. Freeman and Co., page 91 (2007).)

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

The term "anti-HER2 antibody" according to the invention is an antibody that binds specifically to HER2 antigen.

As defined herein, the terms "trastuzumab", "HERCEPTIN®" and "huMAb4D5-8" are used interchangeably. Such antibody preferably comprises the light and heavy chain amino acid sequences shown in FIG. 13 (SEQ ID NO: 1) and FIG. 14 (SEQ ID NO: 2), respectively.

The "epitope 4D5" or "4D5 epitope" or "4D5" is the region in the extracellular domain of HER2 to which the antibody 4D5 (ATCC CRL 10463) and trastuzumab bind. This epitope is close to the transmembrane domain of HER2, and within Domain IV of HER2. To screen for antibodies which bind to the 4D5 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 529 to about residue 625, inclusive, of HER2).

The "epitope 2C4" or "2C4 epitope" is the region in the extracellular domain of HER2 to which the antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of HER2. Epitope 2C4 comprises residues from domain II in the extracellular domain of HER2. The 2C4 antibody and Pertuzumab bind to the extracellular domain of HER2 at the junction of domains I, II and III (Franklin et al. Cancer Cell 5:317-328 (2004)).

As defined herein, the terms "T-DM1," "trastuzumab-MCC-DM1," "ado-trastuzumab emtansine," "trastuzumab emtansine," and "KADCYLA®" are used interchangeably, and refer to trastuzumab linked through the linker moiety MCC to the maytansinoid drug moiety DM1, including all mixtures of variously loaded and attached antibody-drug conjugates where 1, 2, 3, 4, 5, 6, 7, and 8 drug moieties are covalently attached to the antibody trastuzumab (U.S. Pat. No. 7,097,840; US 2005/0276812; US 2005/0166993).

The term "Bcl-2" as used herein refers to the Bcl-2 protein (Swiss Prot ID No. P10415), a member of the Bcl-2 family of proteins (Cory, S., and Adams, J. M., Nature Reviews Cancer 2 (2002) 647-656; Adams, Genes und Development 17 (2003) 2481-2495; Danial, N. N., and Korsmeyer, S. J., Cell 116 (2004) 205-219; Petros, A. M., Biochim Biophys Acta 1644 (2004) 83-94).

The term "selective Bcl-2 inhibitor" as used herein refers to polypeptides and small molecules inhibiting prosurvival members of the Bcl-2 family of proteins. Preferably, the selective Bcl-2 inhibitor is 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide, (a.k.a. ABT-199 or GDC-0199), or a pharmaceutically acceptable salt thereof, a Bcl-2 inhibitor of formula I, which is described in International Publication No. WO2010/0138588 and in US publication No. US2010/0305122, which are incorporated by reference herein.

Formula I

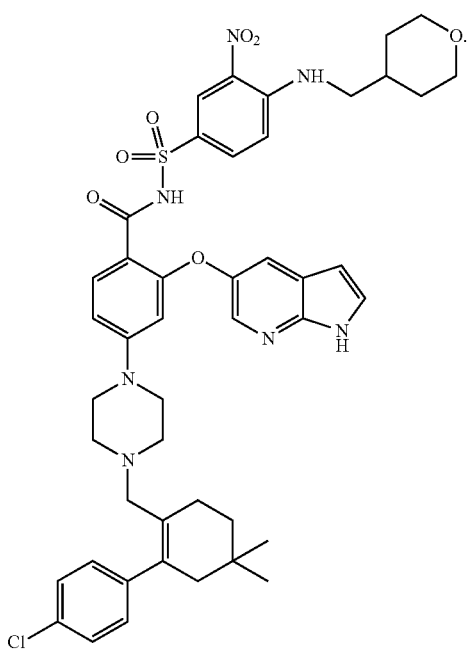

2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide Herein, an "anti-tumor agent" refers to a drug used to treat cancer. Non-limiting examples of anti-tumor agents herein include chemotherapy agents, HER dimerization inhibitors, HER antibodies, antibodies directed against tumor associated antigens, anti-hormonal compounds, cytokines, EGFR-targeted drugs, anti-angiogenic agents, tyrosine kinase inhibitors, growth inhibitory agents and antibodies, cytotoxic agents, antibodies that induce apoptosis, COX inhibitors, farnesyl transferase inhibitors, antibodies that binds oncofetal protein CA 125, HER2 vaccines, Raf or ras inhibitors, liposomal doxorubicin, topotecan, taxane, dual tyrosine kinase inhibitors, TLK286, EMD-7200, pertuzumab, trastuzumab, erlotinib, and bevacizumab.

A "chemotherapy" is use of a chemotherapeutic agent useful in the treatment of cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine,dichloroplatinum(II), CAS No. 15663-27-1), carboplatin (CAS No. 41575-94-4), paclitaxel (TAXOL®, Bristol-Myers Squibb Oncology, Princeton, N.J.), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTU-BAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (T-2 toxin, verracurin A, roridin A and anguidine); urethan; vindesine; dacarbazine; mannomustine; mitobronitol; mitolactol; pipobroman; gacytosine; arabinoside (Ara-C); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include breast cancer, squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. In a preferred embodiment, the cancer is breast cancer. In another preferred embodiment, the cancer is gastric cancer.

Reference to a tumor or cancer as a "Stage 0," "Stage I," "Stage II," "Stage III," or "Stage IV", and various sub-stages within this classification, indicates classification of the tumor or cancer using the Overall Stage Grouping or Roman Numeral Staging methods known in the art. Although the actual stage of the cancer is dependent on the type of cancer, in general, a Stage 0 cancer is an in situ lesion, a Stage I cancer is small localized tumor, a Stage II and III cancer is a local advanced tumor which exhibits involvement of the local lymph nodes, and a Stage IV cancer represents metastatic cancer. The specific stages for each type of tumor is known to the skilled clinician.

The term "metastatic breast cancer" means the state of breast cancer where the cancer cells are transmitted from the original site to one or more sites elsewhere in the body, by the blood vessels or lymphatics, to form one or more secondary tumors in one or more organs besides the breast.

An "advanced" cancer is one which has spread outside the site or organ of origin, either by local invasion or metastasis. Accordingly, the term "advanced" cancer includes both locally advanced and metastatic disease.

A "refractory" cancer is one which progresses even though an anti-tumor agent, such as a chemotherapy, is being administered to the cancer patient. An example of a refractory cancer is one which is platinum refractory.

A "recurrent" cancer is one which has regrown, either at the initial site or at a distant site, after a response to initial therapy, such as surgery.

A "locally recurrent" cancer is cancer that returns after treatment in the same place as a previously treated cancer.

An "operable" or "resectable" cancer is cancer which is confined to the primary organ and suitable for surgery (resection).

A "non-resectable" or "unresectable" cancer is not able to be removed (resected) by surgery.

The terms "HER2-positive" and "HER2 expressing" are used herein interchangeably. A "HER2-positive" cancer comprises cancer cells which have higher than normal levels of HER2. Examples of HER2-positive cancer include HER2-positive breast cancer and HER2-positive gastric cancer. Optionally, HER2-positive is a HER2 overexpressing cancer, and in certain embodiments the HER-2 positive cancer has an immunohistochemistry (IHC) score of 2+ or 3+ and/or an in situ hybridization (ISH) amplification ratio $\geq 2.0$.

In situ hybridization (ISH) determines the number of her2 copies using a DNA probe coupled to a fluorescent, chromogenic, or silver detection system (ie, FISH, CISH, or SISH), or a combination of CISH and SISH systems (brightfield double ISH (BDISH) or dual-hapten, dual-color ISH (DDISH)). ISH may be conducted using a single probe to enumerate her2 copies per nucleus only or as a dual-probe technique where hybridization of a chromosome 17 centromere probe (chromosome enumeration probe 17, CEP17) allows determination of the her2:CEP17 ratio. The two-probe approach may be performed as a dual-color technique, with cohybridization of the two probes on the same slide, or as a monochrome assay where each probe is used on sequential slides. The her2:CEP17 ratio is sometimes regarded as a better reflection of her2 amplification status than mean her2 copy number, as the latter is also dependent on other parameters, such as the mitotic index of the tumor, section thickness, nuclear truncation effects, and abnormal chromosome copy number (aneusomy). The phrase "in situ hybridization (ISH) amplification ratio $\geq 2.0$" refers to her2:CEP17 ratio $\geq 2.0$. For further details see, e.g. Sauter G, et al. Guidelines for human epidermal growth factor receptor 2 testing: biologic and methodologic considerations. *J Clin Oncol* 2009; 27:1323-1333, and the review article by Hanna et al. *Modern Pathology* (2014) 27, 4-18.

Herein, a "patient" or "subject" is a human patient. The patient may be a "cancer patient," i.e. one who is suffering or at risk for suffering from one or more symptoms of cancer, in particular gastric or breast cancer.

A "patient population" refers to a group of cancer patients. Such populations can be used to demonstrate statistically significant efficacy and/or safety of a drug, such as Pertuzumab.

A "relapsed" patient is one who has signs or symptoms of cancer after remission. Optionally, the patient has relapsed after adjuvant or neoadjuvant therapy.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

The term "synergistic" as used herein refers to a therapeutic combination which is more effective than the additive effects of the two or more single agents. A determination of a synergistic interaction between an anti-Her2 antibody-dug conjugate, such as trastuzumab-MCC-DM1, and a selective Bcl-2 inhibitor may be based on the results obtained from the assays described herein, or in other assay systems known in the art, utilizing a standard programs for quantifying synergism, additivism, and antagonism among anticancer agents. The program preferably utilized is that described by Chou and Talalay, in "New Avenues in Developmental Cancer Chemotherapy," Academic Press, 1987, Chapter 2. Combination Index (CI) values less than 0.8 indicate synergy, values greater than 1.2 indicate antagonism and values between 0.8 to 1.2 indicate additive effects. The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially in time, whereas in combination therapy, effective dosages of two or more active ingredients are administered together.

"Neoadjuvant therapy" or "preoperative therapy" herein refers to therapy given prior to surgery. The goal of neoadjuvant therapy is to provide immediate systemic treatment, potentially eradicating micrometastases that would otherwise proliferate if the standard sequence of surgery followed by systemic therapy were followed. Neoadjuvant therapy may also help to reduce tumor size thereby allowing complete resection of initially unresectable tumors or preserving portions of the organ and its functions. Furthermore, neoadjuvant therapy permits an in vivo assessment of drug efficacy, which may guide the choice of subsequent treatments.

"Adjuvant therapy" herein refers to therapy given after definitive surgery, where no evidence of residual disease can be detected, so as to reduce the risk of disease recurrence. The goal of adjuvant therapy is to prevent recurrence of the cancer, and therefore to reduce the chance of cancer-related death. Adjuvant therapy herein specifically excludes neoadjuvant therapy.

"Definitive surgery" is used as that term is used within the medical community. Definitive surgery includes, for example, procedures, surgical or otherwise, that result in removal or resection of the tumor, including those that result in the removal or resection of all grossly visible tumor. Definitive surgery includes, for example, complete or curative resection or complete gross resection of the tumor.

Definitive surgery includes procedures that occur in one or more stages, and includes, for example, multi-stage surgical procedures where one or more surgical or other procedures are performed prior to resection of the tumor. Definitive surgery includes procedures to remove or resect the tumor including involved organs, parts of organs and tissues, as well as surrounding organs, such as lymph nodes, parts of organs, or tissues. Removal may be incomplete such that tumor cells might remain even though undetected.

"Survival" refers to the patient remaining alive, and includes disease free survival (DFS), progression free survival (PFS) and overall survival (OS). Survival can be estimated by the Kaplan-Meier method, and any differences in survival are computed using the stratified log-rank test.

"Progression-Free Survival" (PFS) is the time from the first day of treatment to documented disease progression (including isolated CNS progression) or death from any cause on study, whichever occurs first.

"Disease free survival (DFS)" refers to the patient remaining alive, without return of the cancer, for a defined period of time such as about 1 year, about 2 years, about 3 years, about 4 years, about 5 years, about 10 years, etc., from initiation of treatment or from initial diagnosis. In one aspect of the invention, DFS is analyzed according to the intent-to-treat principle, i.e., patients are evaluated on the basis of their assigned therapy. The events used in the analysis of DFS can include local, regional and distant recurrence of cancer, occurrence of secondary cancer, and death from any cause in patients without a prior event (e.g, breast cancer recurrence or second primary cancer).

"Overall survival" refers to the patient remaining alive for a defined period of time, such as about 1 year, about 2 years, about 3 years, about 4 years, about 5 years, about 10 years, etc., from initiation of treatment or from initial diagnosis. In the studies underlying the invention the event used for survival analysis was death from any cause.

By "extending survival" is meant increasing DFS and/or OS in a treated patient relative to an untreated patient, or relative to a control treatment protocol. Survival is monitored for at least about six months, or at least about 1 year, or at least about 2 years, or at least about 3 years, or at least about 4 years, or at least about 5 years, or at least about 10 years, etc., following the initiation of treatment or following the initial diagnosis.

"Hazard ratio" in survival analysis is a summary of the difference between two survival curves, representing the reduction in the risk of death on treatment compared to control, over a period of follow-up. Hazard ratio is a statistical definition for rates of events. For the purpose of the invention, hazard ratio is defined as representing the probability of an event in the experimental arm divided by the probability of an event in the control arm at any specific point in time.

By "monotherapy" is meant a therapeutic regimen that includes only a single therapeutic agent for the treatment of the cancer or tumor during the course of the treatment period.

The terms "treat" and "treatment" refer to both therapeutic treatment and prophylactic or preventative measures, wherein the object is to prevent or slow down (lessen) an undesired physiological change or disorder, such as the growth, development or spread of a hyperproliferative condition, such as cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "a method of treating" or its equivalent, when applied to, for example, cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed to induce an overall beneficial course of action.

The terms "co-administration" or "co-administering" refer to the administration of the anti-HER2 antibody-drug conjugate and the selective Bcl-2 inhibitor as two separate formulations. The co-administration can be simultaneous or sequential in either order. In one further embodiment, there is a time period while both (or all) active agents simultaneously exert their biological activities. The anti-HER2 antibody-drug conjugate and the selective Bcl-2 inhibitor are co-administered either simultaneously or sequentially (e.g. via an intravenous (i.v.) through a continuous infusion (one for the antibody-drug conjugate and eventually one for the Bcl-2 inhibitor; or the Bcl-2 inhibitor is administered orally). When both therapeutic agents are co-administered sequentially the agents are administered in two separate administrations that are separated by a "specific period of time". The term specific period of time is meant anywhere from 1 hour to 15 days. For example, one of the agents can be administered within about 15, 14, 13, 12, 11, 10, 9, 8, 7, 6, 5, 4, 3, 2, or 1 day, or 24, 23, 22, 21, 20, 19, 18, 17, 16, 15, 14, 13, 12, 11, 10, 9, 8, 7, 6, 5, 4, 3, 2 or 1 hour from the administration of the other agent, and, in one embodiment, the specific period time is 10, 9, 8, 7, 6, 5, 4, 3, 2, or 1 day, or 24, 23, 22, 21, 20, 19, 18, 17, 16, 15, 14, 13, 12, 11, 10, 9, 8, 7, 6, 5, 4, 3, 2 or 1 hour.

The term "simultaneously" means at the same time or within a short period of time, usually less than 1 hour.

A drug that is administered "concurrently" with one or more other drugs is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

A dosing period as used herein is meant a period of time, during which each therapeutic agent has been administered at least once. A dosing cycle is usually about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days.

In certain embodiments, a dosing cycle is for 21 days.

In certain embodiments of a method of treating cancer in a patient as provided herein, the method comprises administering the anti-HER2 antibody-drug conjugate and the selective Bcl-2 inhibitor for one or more dosing cycles to the patient. In one embodiment, the one or more dosing cycles each last for at least one week. In another embodiment, the one or more dosing cycles are each for at least two weeks, three weeks, four weeks, five weeks, six weeks, seven weeks, eight weeks, nine weeks, or for more than nine weeks. In one embodiment, each dosing cycle is three weeks.

In a preferred embodiment, the antibody-drug conjugate is administered as an intravenous (i.v.) infusion every three weeks (21-day cycle).

In another preferred embodiment, the antibody-drug conjugate is KADCYLA® (ado-trastuzumab emtansine), which is administered as a 3.6 mg/kg i.v. infusion every 3 weeks (21-day cycle).

In some embodiments of the method of treatment provided herein, the selective Bcl-2 inhibitor is 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl) benzamide (GDC-0199). In certain embodiments, the amount of GDC-0199 administered to the patient per dose is increased during the first dosing cycle from initial amounts of between 10 mg to 80 mg to final amounts of between 190 mg to 400 mg. In certain embodiments, the amount of GDC-0199 per dose administered to the patients begins with 50 mg or 100 mg, and is increased to 300 mg per dose. In some embodiments, the amount of GDC-0199 in the initial doses administered to the patient can, for example, be between 20 mg to 60 mg (e.g., 20 mg, 25 mg, 30 mg, 35 mg, 40 mg, 45 mg, 50 mg, 55 mg or 60 mg doses), followed by dose amounts of 100 mg, 200 mg, 300 mg or more of GDC-0199.

An "adverse event" is any unfavorable and unintended sign, symptom, or disease temporally associated with the use of an investigational (medicinal) product or other protocol-imposed intervention, regardless of attribution; and includes: adverse events (AEs) not previously observed in the patient that emerge during the protocol-specified AE reporting period, including signs or symptoms associated with breast cancer that were not present before the AE reporting period; complications that occur as a result of protocol-mandated interventions (e.g., invasive procedures such as biopsies); if applicable, AEs that occur before assignment of study treatment associated with medication washout, no treatment run-in, or other protocol-mandated intervention; Preexisting medical conditions (other than the condition being studied) judged by the investigator to have worsened in severity or frequency or changed in character during the protocol-specified AE reporting period.

It is self-evident that the antibody-drug conjugates are administered to the patient in a "therapeutically effective amount" (or simply "effective amount") which is the amount of the respective compound or combination that will elicit the biological or medical response of a tissue, system, animal or human that is being sought by the researcher, veterinarian, medical doctor or other clinician. The administration of an effective amount of a therapeutically agent can be a single administration or split dose administration. "split dose administration" is meant an effective amount is a split into multiple doses, preferably 2, and administered within 1 or 2 days. For example, if 100 mg of a selective Bcl-2 inhibitor is deemed effective, it can be administered in one 100 mg administration or two 50 mg administrations. Split dose administration is sometimes desirable at the beginning of a dosing period to reduce side effects. When an effective amount is administered in split dosing, it is still considered one administration of an effective amount. For example, when 100 mg is the effective amount of a selective Bcl-2 inhibitor and that amount is administered in two 50 mg doses over a period of time, e.g. 2 days, only one effective amount is administered during that period of time.

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m$^2$ dose, but rather as an absolute amount of the therapeutic agent.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks, preferably every 3 weeks.

"Infusion" or "infusing" refers to the introduction of a drug-containing solution into the body through a vein for therapeutic purposes. Generally, this is achieved via an intravenous (IV) bag.

An "intravenous bag" or "IV bag" is a bag that can hold a solution which can be administered via the vein of a patient. In one embodiment, the solution is a saline solution (e.g. about 0.9% or about 0.45% NaCl). Optionally, the IV bag is formed from polyolefin or polyvinyl chloride.

In the context of this invention, additional other cytotoxic, chemotherapeutic or anti-cancer agents, or compounds that enhance the effects of such agents (e.g. cytokines) may be used in the anti-HER2 antibody-drug conjugate and Bcl-2 inhibitor combination treatment of HER2 expressing cancer. Such molecules are suitably present in combination in amounts that are effective for the purpose intended. Preferably the anti-HER2 antibody-drug conjugate and Bcl-2 inhibitor combination treatment is used without such additional cytotoxic, chemotherapeutic or anti-cancer agents, or compounds that enhance the effects of such agents.

Such agents include, for example: alkylating agents or agents with an alkylating action, such as cyclophosphamide (CTX; e.g. CYTOXAN®), chlorambucil (CHL; e.g. LEUKERAN®), cisplatin (CisP; e.g. PLATINOL®) busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP16; e.g. VEPESID®), 6-mercaptopurine (6MP), 6-thioguanine (6TG), cytarabine (Ara-C), 5-fluorouracil (5-FU), capecitabine (e.g. XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and paclitaxel derivatives, the cytostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin and other folic acid derivatives, and similar, diverse antitumor agents.

The following agents may also be used as additional agents: arnifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil. Preferably the type II anti-CD20 antibody and Bcl-2 inhibitor combination treatment is used without such additional agents.

The use of the cytotoxic and anticancer agents described above as well as antiproliferative target-specific anticancer drugs like protein kinase inhibitors in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

In the context of this invention, an effective amount of ionizing radiation may be carried out and/or a radiopharmaceutical may be used in addition to the anti-HER2 antibody-drug conjugate and Bcl-2 inhibitor combination treatment. The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Is also possible to label the antibody with such radioactive isotopes. Preferably the type II anti-CD20 antibody and Bcl-2 inhibitor combination treatment is used without such ionizing radiation.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination of the invention is enhanced when combined with radiation, optionally with additional chemotherapeutic or anticancer agents. Parameters of adjuvant radiation therapies are, for example, contained in WO 99/60023.

The anti-HER2 antibody-drug conjugates are administered to a patient according to known methods, by intravenous administration as a bolus or by continuous infusion over a period of time, by intramuscular, intraperitoneal, intracerobrospinal, subcutaneous, intra-articular, intrasynovial, or intrathecal routes. Intravenous or subcutaneous administration of the antibodies is preferred.

The Bcl-2 inhibitors are administered to a patient according to known methods, e.g. by intravenous administration as a bolus or by continuous infusion over a period of time, by intramuscular, intraperitoneal, intracerobrospinal, subcutaneous, intra-articular, intrasynovial, intrathecal, or peroral routes. Intravenous, subcutaneous or oral administration of the Bcl-2 inhibitors is preferred.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

A "vial" is a container suitable for holding a liquid or lyophilized preparation. In one embodiment, the vial is a single-use vial, e.g. a 20-cc single-use vial with a stopper.

The term "package insert" is used to refer to instructions customarily included in commercial packages of therapeutic products, that contain information about the indications, usage, dosage, administration, contraindications and/or warnings concerning the use of such therapeutic products.

Trastuzumab-MCC-DM1 (T-DM1: KADCYLA®, Ado-Trastuzumab Emtansine)

The present invention includes therapeutic combinations comprising trastuzumab-MCC-DM1 which has the structure:

where Tr is trastuzumab, and p is an integer from 1 to 8. The drug to antibody ratio or drug loading is represented by p in the above structure of trastuzumab-MCC-DM1. The drug loading value p is 1 to 8. Trastuzumab-MCC-DM1 includes all mixtures of variously loaded and attached antibody-drug conjugates where 1, 2, 3, 4, 5, 6, 7, and 8 drug moieties are covalently attached to the antibody trastuzumab.

Trastuzumab is produced by a mammalian cell (Chinese Hamster Ovary, CHO) suspension culture. The HER2 (or c-erbB2) proto-oncogene encodes a transmembrane receptor protein of 185 kDa, which is structurally related to the epidermal growth factor receptor. HER2 protein overexpression is observed in 25%-30% of primary breast cancers and can be determined using an immunohistochemistry based assessment of fixed tumor blocks (Press M F, et al (1993) Cancer Res 53:4960-70. Trastuzumab is an antibody that has antigen binding residues of, or derived from, the murine 4D5 antibody (ATCC CRL 10463, deposited with American Type Culture Collection, 12301 Parklawn Drive, Rockville, Md. 20852 under the Budapest Treaty on May 24, 1990). Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as in U.S. Pat. No. 5,821,337.

The antibody-drug conjugate, trastuzumab-MCC-DM1, comprises a maytansinoid drug moiety DM1 (U.S. Pat. No. 5,208,020; 6,441,163) and may be prepared from ansamitocin fermentation products (U.S. Pat. No. 6,790,954; US 2005/0170475).

Selective Bcl-2 Inhibitors

In a preferred embodiment, the selective Bcl-2 inhibitor of the present invention is 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide, (a.k.a. ABT-199 or GDC-0199), a Bcl-2 inhibitor of formula I, which is described in International Publication No. WO2010/0138588 and in US publication NO. US2010/0305122, which are incorporated by reference herein.

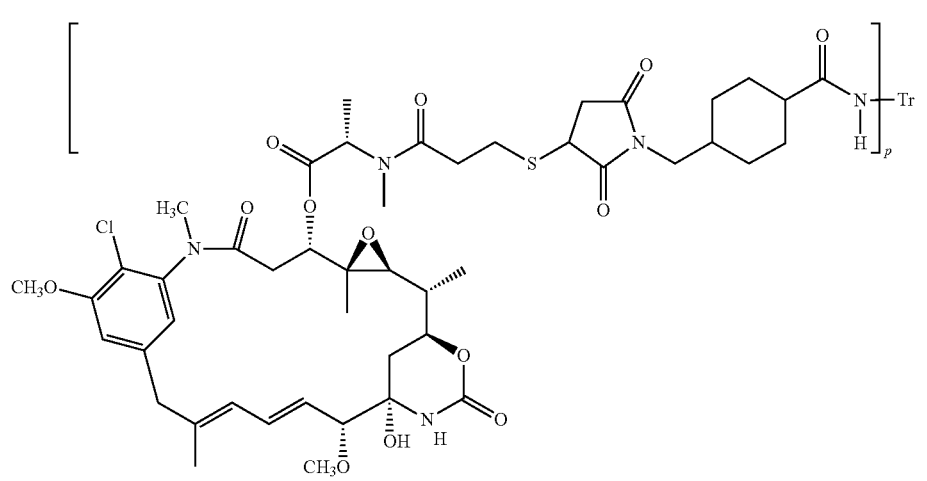

Formula II

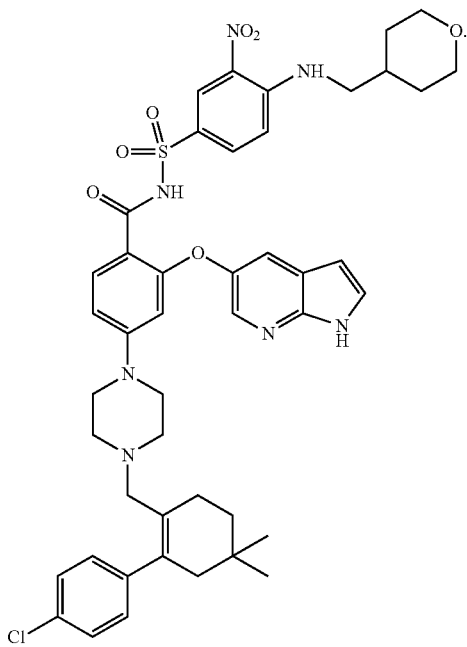

Formula I 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide Other selective Bcl-2 inhibitors include, for example, Oblimersen, SPC-2996, RTA-402, Gossypol, AT-101, Obatoclax mesylate, A-371191, A-385358, A-438744, ABT-737, ABT-263, AT-101, BL-11, BL-193, GX-15-003, 2-Methoxyantimycin $A_3$, HA-14-1, KF-67544, Purpurogallin, TP-TW-37, YC-137 and Z-24, described e.g. in Zhai, D., et al., Cell Death and Differentiation 13 (2006) 1419-1421.

Pharmaceutical Compositions

Pharmaceutical compositions or formulations of the present invention include combinations of trastuzumab-MCC-DM1, a selective Bcl-2 inhibitor, and one or more pharmaceutically acceptable carrier, glidant, diluent, or excipient.

Trastuzumab-MCC-DM1 and selective Bcl-2 inhibitors of the present invention may exist in unsolvated as well as solvated forms with pharmaceutically acceptable solvents such as water, ethanol, and the like, and it is intended that the invention embrace both solvated and unsolvated forms.

Trastuzumab-MCC-DM1 and selective Bcl-2 inhibitors of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Pharmaceutical compositions encompass both the bulk composition and individual dosage units comprised of more than one (e.g., two) pharmaceutically active agents including trastuzumab-MCC-DM1 and a selective Bcl-2 inhibitor selected from the lists of the additional agents described herein, along with any pharmaceutically inactive excipients, diluents, carriers, or glidants. The bulk composition and each individual dosage unit can contain fixed amounts of the aforesaid pharmaceutically active agents. The bulk composition is material that has not yet been formed into individual dosage units. An illustrative dosage unit is an oral dosage unit such as tablets, pills, capsules, and the like. Similarly, the herein-described method of treating a patient by administering a pharmaceutical composition of the present invention is also intended to encompass the administration of the bulk composition and individual dosage units.

Pharmaceutical compositions also embrace isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^3H$ and $^{14}C$) are useful in compound and/or substrate tissue distribution assays. Tritiated ($^3H$) and carbon-14 ($^{14}C$) isotopes are useful for their ease of preparation and detectability. Further, substitution with heavier isotopes such as deuterium ($^2H$) may afford certain therapeutic advantages resulting from greater metabolic stability (e.g., increased in vivo half-life or reduced dosage requirements) and hence may be preferred in some circumstances. Positron emitting isotopes such as $^{15}I$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Trastuzumab-MCC-DM1 and selective Bcl-2 inhibitors may be formulated in accordance with standard pharmaceutical practice for use in a therapeutic combination for therapeutic treatment (including prophylactic treatment) of hyperproliferative disorders in mammals including humans. The invention provides a pharmaceutical composition comprising trastuzumab-MCC-DM1 in association with one or more pharmaceutically acceptable carrier, glidant, diluent, or excipient.

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration with pharmaceutically acceptable diluents, carriers, excipients or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, ethanol, or benzylalcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, including Tween 80, PLURONICS™ or polyethylene glycol (PEG), including PEG400. The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences 18$^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

As a general proposition, the initial pharmaceutically effective amount of trastuzumab-MCC-DM1 administered per dose will be in the range of about 0.01-100 mg/kg, namely about 0.1 to 20 mg/kg of patient body weight per day, with the typical initial range of compound used being 0.3 to 15 mg/kg/day.

In a preferred embodiment, trastuzumab-MCC-DM1 is formulated as a lyophilized poweder in single-use vials containing 100 mg per vial or 160 mg per vial, and is administered at a dose of 3.6 mg/kg as an intravenous infusion every 3 weeks.

Pharmaceutical compositions of the anti-Bcl-2 active agent alone, e.g. the Bcl-2 inhibitor, depend on their pharmaceutical properties; e.g. for small chemical compounds such as e.g. ABT-737, ABT-199 or ABT-263, one formulation could be e.g. the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |

-continued

| Item | Ingredients | mg/tablet | | | |
|---|---|---|---|---|---|
| 4. | Microcrystalline Cellulose | 30 | 30 | 30 | 150 |
| 5. | Magnesium Stearate | 1 | 1 | 1 | 1 |
|  | Total | 167 | 167 | 167 | 831 |

Manufacturing Procedure:

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
|  | Total | 200 | 200 | 300 | 600 |

Manufacturing Procedure:

1. Mix items 1, 2 and 3 in a suitable mixer for 30 minutes.
2. Add items 4 and 5 and mix for 3 minutes.
3. Fill into a suitable capsule.

The active ingredients may also be entrapped in microcapsules prepared, for example, by coacervation techniques or by interracial polymerization, for example, hydroxymethylcellulose or gelatin-microcapsules and poly-(methyl-methacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The formulations to be used for in vivo administration must be sterile. This is readily accomplished by filtration through sterile filtration membranes.

The following examples, sequence listing and figures are provided to aid the understanding of the present invention, the true scope of which is set forth in the appended claims. It is understood that modifications can be made in the procedures set forth without departing from the spirit of the invention.

EXAMPLES

Example 1

Expression of Bcl-2 Family Pro-Survival Molecules in T-DM1-Resistant Breast Cancer Cells Preparation of T-DM1 Resistant Cell Lines Initally, KPL-4 and BT-474M1 cells were made resistant to T-DM1 by continuous culture in the presence of T-DM1, starting at a very low concentration of 10 ng/mL, which was gradually increased to 2 µg/mL. The cells derived are the "resistant pools" which were maintained in culture in 2 µg/mL T-DM1. To derive stably resistant clones, each pool (KPL-4 and BT-474M1) was subjected to single cell sorting and cloning. Clones were maintained without T-DM1 such that clones that had stable resistance in the absence of T-DM1 could be identified.

TaqMan analysis

Total RNA was prepared using Qiagen RNeasy Mini kit. Genomic DNA was removed by DNase I. Gene expression was quantified using real time quantitative PCR (qPCR or TaqMan). TaqMan One-Step Universal Master Mix (Applied Biosystems) was used for all reactions. The reaction was performed in a standard 96-well plate format with ABI 7500 Real-Time qPCR System. 100 ng total RNA was used as template in each reaction. For data analysis, raw Ct was normalized to house-keeping gene HP1BP3.

Figure 1A:
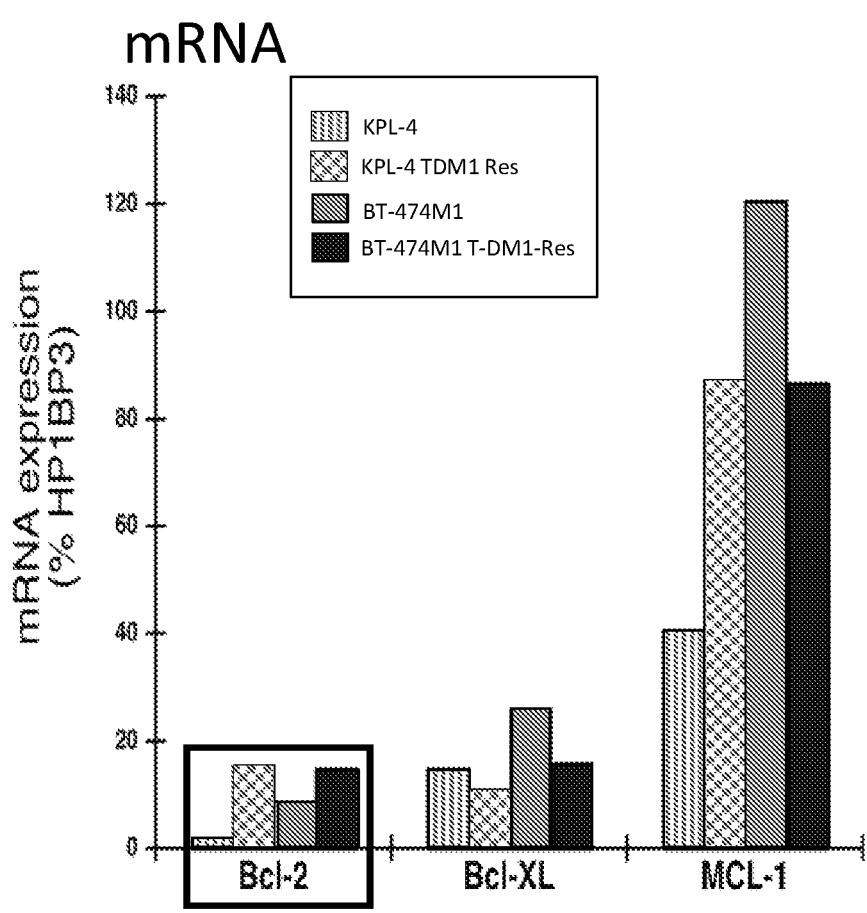
FIGS. 1A and 1B show expression of Bcl-2 family pro-survival molecules in T-DM1 resistant KPL-4 and BT-474M1 human breast cancer cells (HER2 positive) relative to parental cells.

The results of TaqMan analysis are presented in FIG. 1A. The figure shows that Bcl-2 mRNA expression was increased in T-DM1 resistant KPL-4 and T-DM1 resistant BT-474M1 cell lines (normalized to the housekeeping gene HP1BP3) relative to the parent, non-resistant KPL-4 and BT-474M1 cells.

Figure 1B:
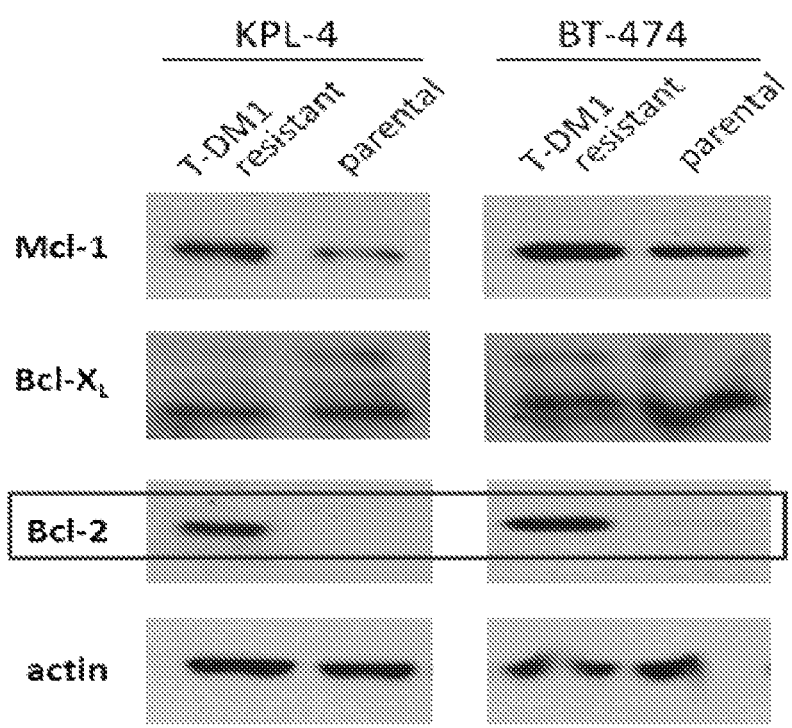

Western blot analysis was performed as follows: Cells were lysed in corrected FLAG elution buffer (CFEB) (19.17 mM Tris (pH 7.5), 916.7 µM MgCl2, 92.5 mM NaCl and 0.1% Triton X-100) with protease and phosphatase inhibitors (Roche); in some cases 6 M urea was added. Cleared lysates were quantitated and equal amounts of proteins were reduced, alkylated, separated by SDS-PAGE, and transferred onto PVDF membranes (Invitrogen) following standard procedures. Western blotting was performed as recommended by the respective antibody manufacturers. Western blot analysis shown in FIG. 1B confirms that Bcl-2 is overexpressed in T-DM1 resistant KPL-4 and BT-474 cell lines.

Example 2

Cell Proliferation Assay—Parental and T-DM1-Resistant KPL-4 Breast Cancer Cell Lines The cell proliferation assay was performed for 3 days using Cell-Titer Glo reagent. KPL-4 parental breast cancer cells and KPL-4 T-DM1-resistant breast cancer cells, prepared as described in Example 1, were treated with T-DM1, GDC-0199 or a combination of T-DM1 and GDC-0199 at fixed ratios. Synergy was analyzed using the Chou and Talalay Drug Combination Dose-Effect Analysis with CalcuSyn software in order to obtain a Combination Index "CI" (Chou and Talalay (1984) Adv. Enzyme Regul. 22:27-55). CI values of less than 1 indicate synergy, while CI=1 indicated additivity.

Figure 2:
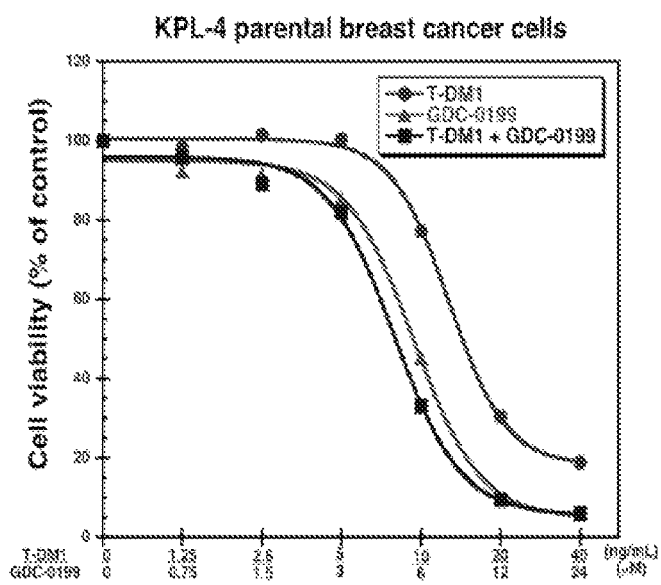
FIG. 2 presents results of a cell viability assay showing that the T-DM1+ GDC-0199 combination has a synergistic effect in KPL-4 T-DM1-resistant human breast cancer cells, while no synergism is observed in KPL-4 parental cells.
Figure 2:
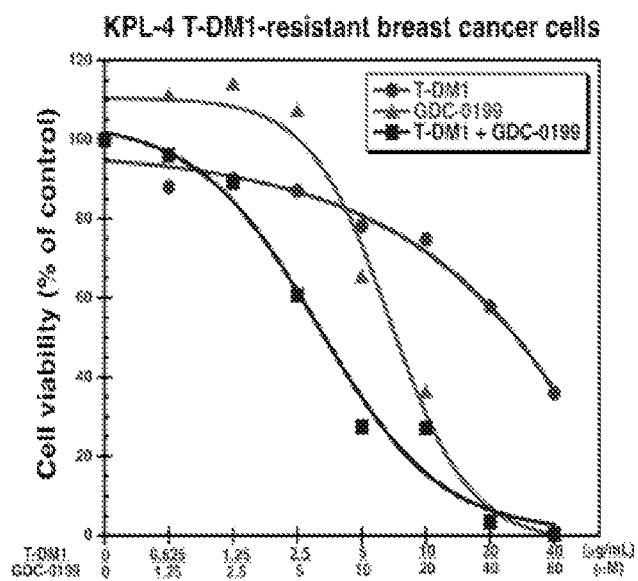

Assay Conditions:

Cells were maintained in Ham's F-12: high glucose DMEM (1:1) supplemented with 10% heat-inactivated fetal bovine serum and 2 mM L-glutamine. Cells were plated in 96-well plates (4000 cells per well for KPL-4 parental cells;

8000 cells per well for KPL-4 T-DM1 resistant cells) and allowed to adhere overnight at 37° C. in a humidified atmosphere of 5% $CO_2$. Medium was then removed and replaced by fresh culture medium containing either T-DM1, GDC-0199, the combination of both. Cell Titer-Glo (Promega Corp.) was added to the wells at 3 days after drug administration and the luminescent signal was measured using EnVision Multilabel Plate Reader (PerkinElmer). Combination Index (C.I.) values were generated using CalcuSyn software (Biosoft, Inc) As shown in FIG. 2, the combination of T-DM1 and GDC-0199 has a synergistic anti-proliferative effect in KPL-4 T-DM1-resistant breast cancer cells.

Example 3

Caspase 3/7 Activation Luminescence Assay—Parental and T-DM1-Resistant KPL-4 Breast Cancer Cell Lines As noted before, the Bcl-2 family of proteins regulates programmed cell death triggered by developmental cues and in response to multiple stress signals. When activated, they can permeabilize the outer membrane of mitochondria and release pro-apoptogenic factors (e.g. cytochrome C) needed to activate the caspases that dismantle the cell (Wang, K., Genes and Development 15 (2001) 2922-2933; (Adams, 2003 supra); Green, D. R., and Kroemer, G., Science 305 (2004) 626-629). Thus, activation of caspases, such as caspases 3 and 7, indicates induction of apoptosis.

In the present experiment, caspase 3/7 activation luminescence assay was performed using the Caspase-Glo® reagent (Promega) essentially following manufacturer's instructions. Assays were performed in the same manner as the viability assays except that drug incubation times were 24 hours and Caspase-Glo 3/7 (Promega) was used to measure apoptosis.

Figure 3:
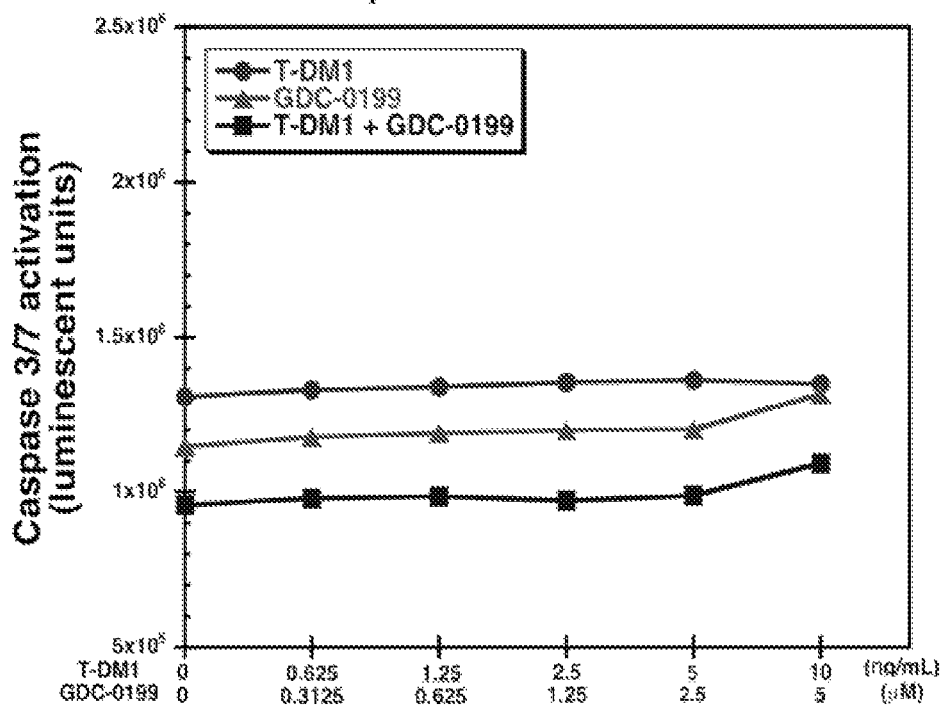
FIG. 3 presents results of a caspase activation assay measuring activation of caspases 3 and 7. The results show that at 24 hours of drug treatment, T-DM1-resistant KPL-4 human breast cancer cells are re-sensitized to T-DM1 in the presence of GDC-0199, whereas at 24 hours, there is no effect of T-DM1+/− GDC-0199 in KPL-4 parental cells.
Figure 3:
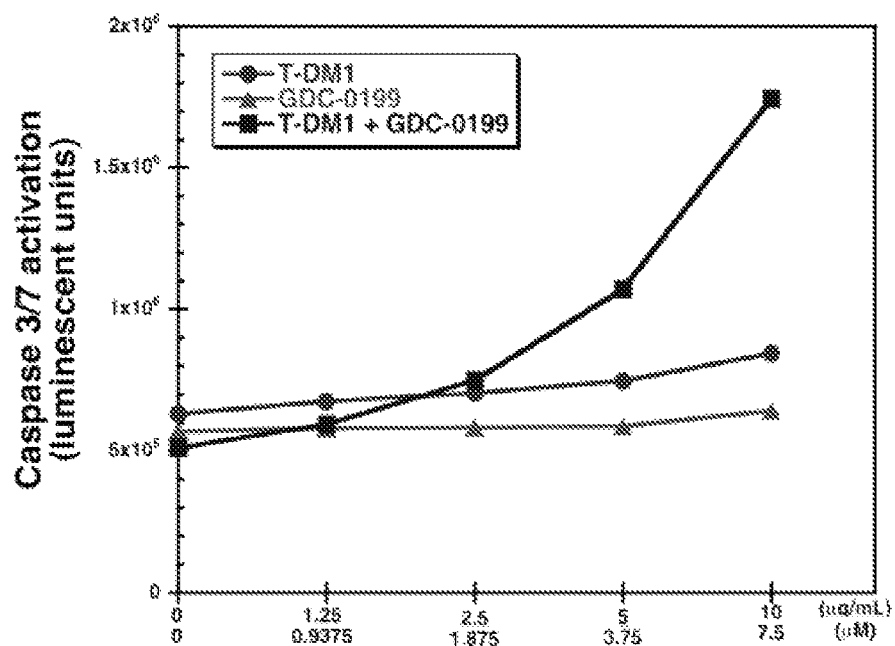

As shown in FIG. 3, right panel, T-DM1-resistant KPL-4 (HER2+) breast cancer cells were re-sensitized to T-DM1 when treated for 24 hours with a combination of T-DM1+ GDC-0199, as shown by increased apoptosis (increased caspase 3/7 activation). The same combination showed no effect in parental cells. It is noted that the results were assessed 24 hours after treatment, which is too early for apoptosis induced by T-DM1 alone in the parental cell line (left panel).

Figure 4A:
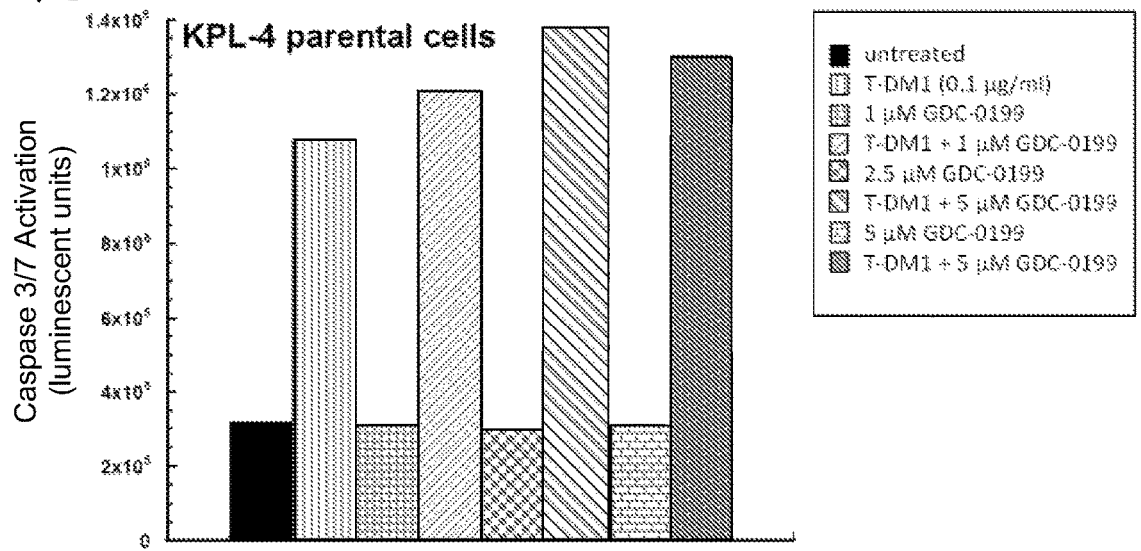
FIGS. 4A and 4B presents the results of a caspase activation assay measuring activation of caspases 3 and 7 in T-DM1 resistant KPL-4 human breast cancer cells relative to parental cells after 48 hours of drug treatment. The results show dose-dependent increases in caspases 3 and 7 activation with the addition of GDC-0199 to T-DM1, with minimal effect of T-DM1 alone. In KPL-4 parental cells, T-DM1 induces robust activation of caspases 3 and 7 with minimal increase upon addition of GDC-0199.
Figure 4A:
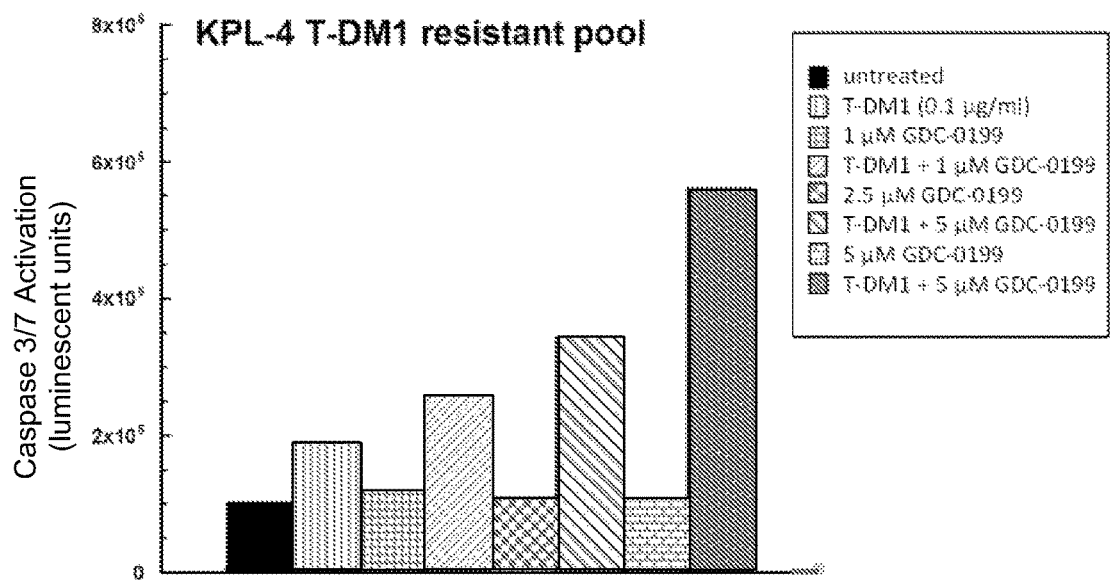
Figure 4B:
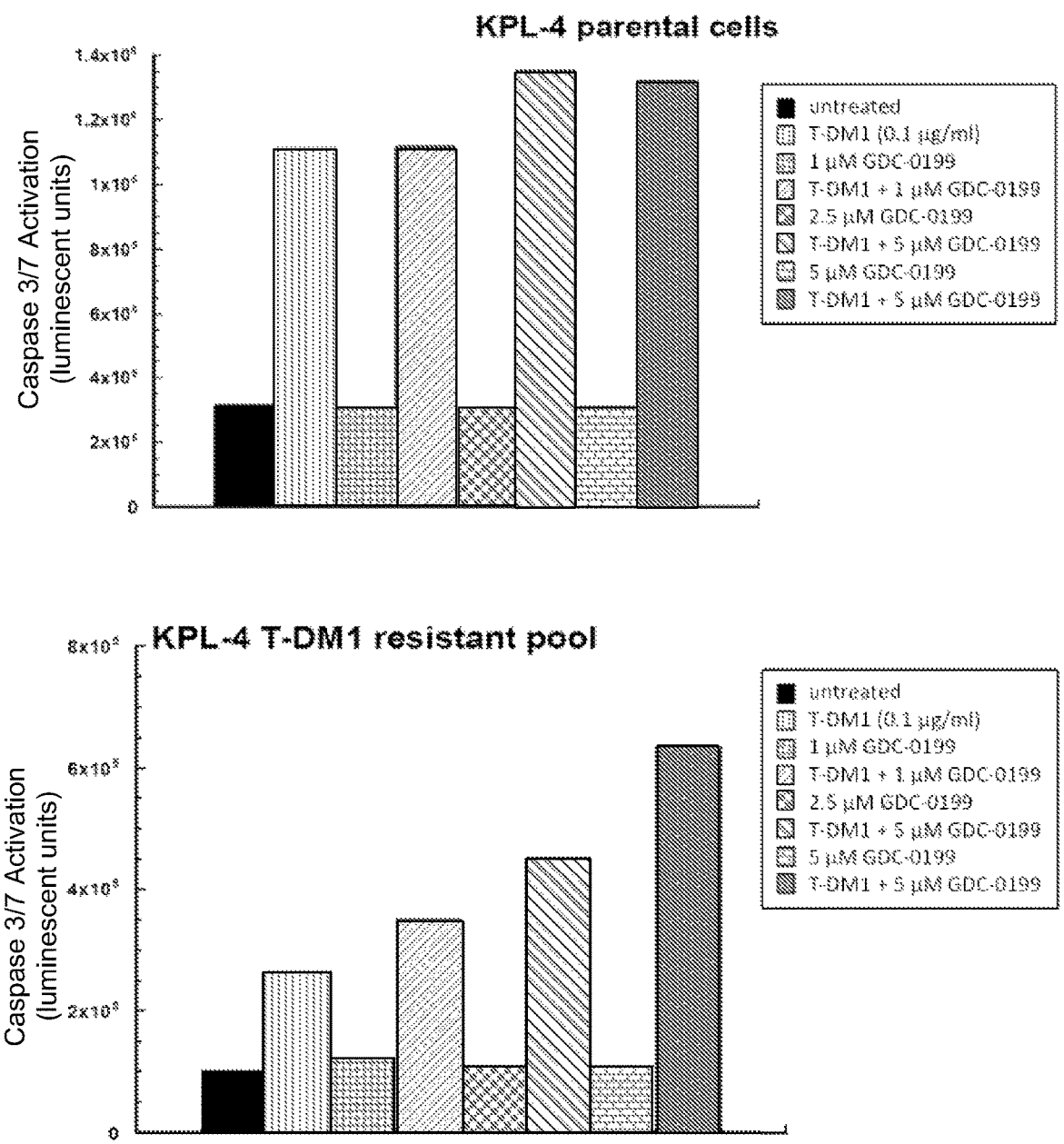

FIGS. 4A and 4B presents the results of a caspase 3/7 activation luminescence in vitro apoptosis assay measuring activation of caspases 3 and 7 in KPL-4 T-DM1-resistant human breast cancer cells relative to parental cells using different concentrations of T-DM1 and GDC-0199, respectively. Increased apoptosis is observed in KPL-4 T-DM1 resistant cells upon the addition of increasing concentrations of GDC-0199 (1, 2.5 or 5 μM) to either 0.1 or 1 μg/mL T-DM1. In contrast, T-DM1 induces robust apoptosis in KPL-4 parental cells which is not further enhanced by the addition of GDC-0199.

Figure 5A:
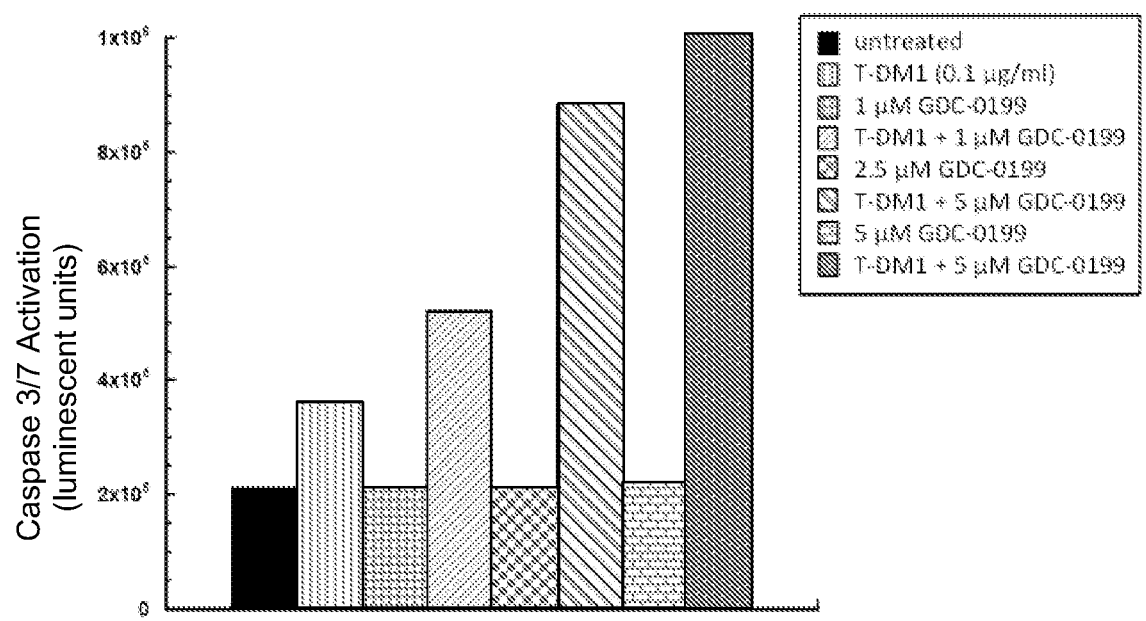
FIG. 5A presents the results of a caspase activation assay measuring activation of caspases 3 and 7 in Clone #17 T-DM1 resistant KPL-4 human breast cancer cell line treated with 1 ug/mL T-DM1 alone or in combination with the indicated doses of GDC-0199 for 48 hours. The results show dose-dependent increases in caspases 3 and 7 activation with the addition of GDC-0199 to T-DM1, with minimal effect of T-DM1 alone.

FIG. 5A presents the results of a caspase 3/7 activation luminescence in vitro apoptosis assay measuring activation of caspases 3 and 7 in Clone #17 T-DM1-resistant KPL-4 human breast cancer cell line treated with T-DM1, GDC-0199 or T-DM1+ GDC-0199. Similar to observations with the KPL-4 T-DM1 resistant pool of cells, induction of apoptosis in Clone #17 was increased upon the addition of increasing concentrations of GDC-0199.

Figure 6A:
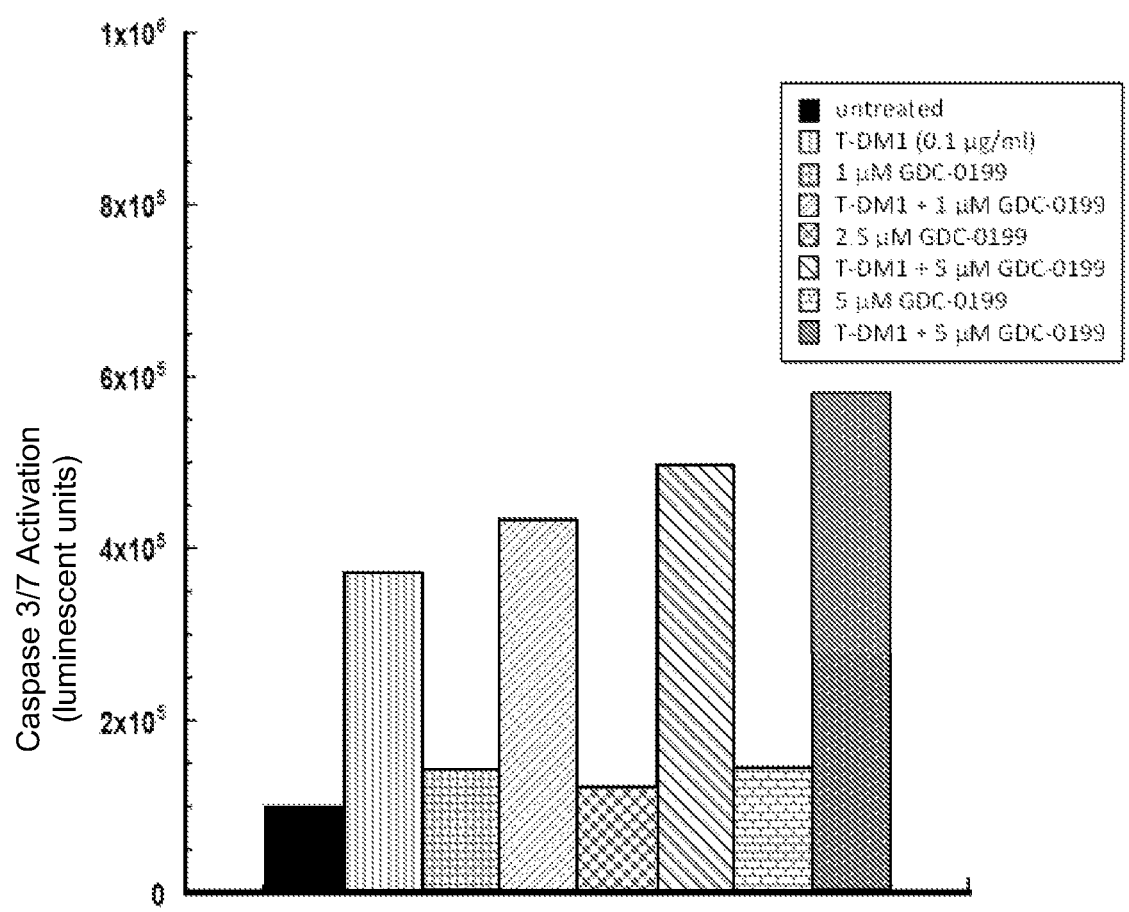
FIGS. 6A and 6B show the results of a caspase activation assay measuring activation of caspases 3 and 7 in Clone #8 T-DM1 resistant KPL-4 human breast cell line at 0.1 µg/mL and 1 µg/mL T-DM1 concentrations, respectively, alone or in combination with the indicated concentrations of GDC-0199.
Figure 6B:
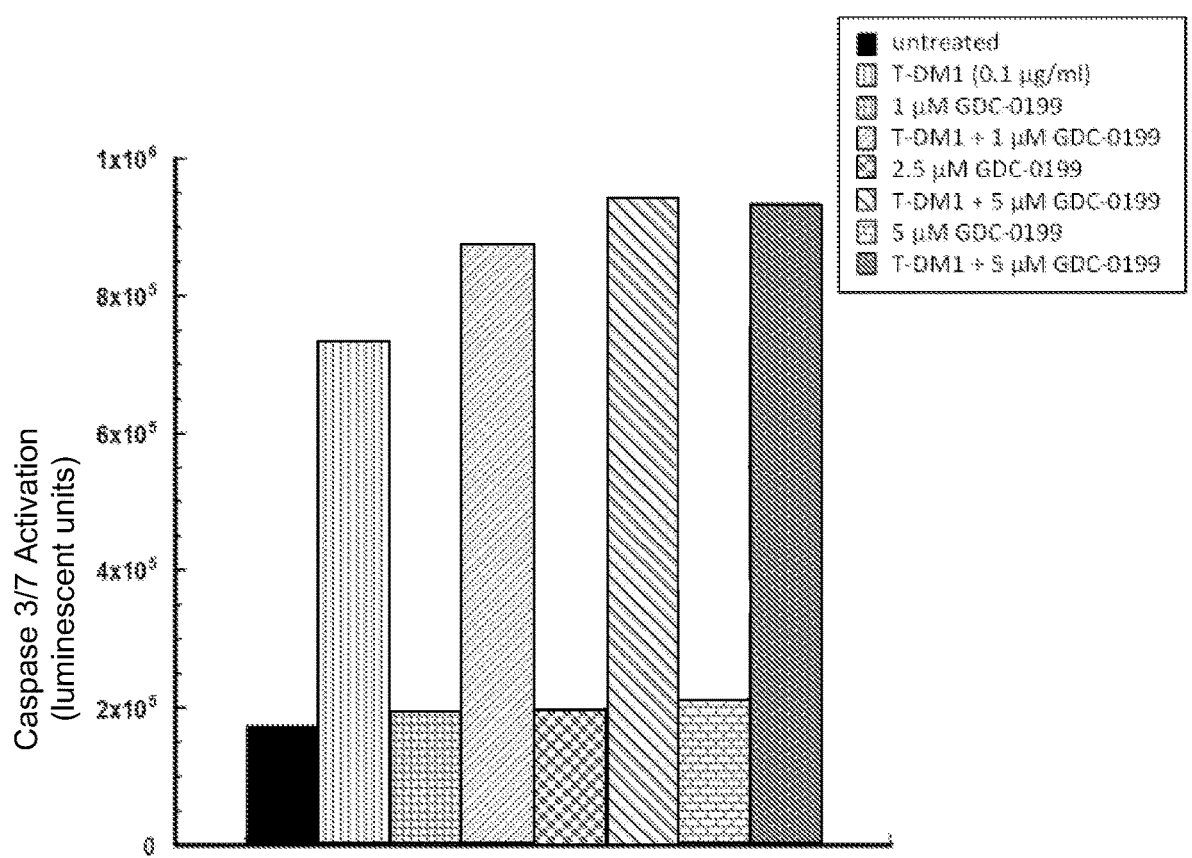

FIGS. 6A and 6B show the results of a caspase 3/7 activation luminescentce in vitro apoptosis assay measuring activation of caspases 3 and 7 in Clone #8 T-DM1 resistant KPL-4 human breast cell line treated with 0.1 μg/mL and 1 μg/mL T-DM1 concentrations, respectively, alone or in combination with the indicated concentrations of GDC-0199.

As shown in FIGS. 4A, 4B, 5A, 6A and 6B, the results obtained with different clones of T-DM1-resistant KPL-4 breast cancer cell lines confirm the enhanced proapoptotic activity of the T-DM-1+ GDC-0199 combination at various concentrations.

Example 4

Xenograft Studies—KPL-4 T-DM1-Resistant Breast Cancer Cell Lines

Figure 5B:
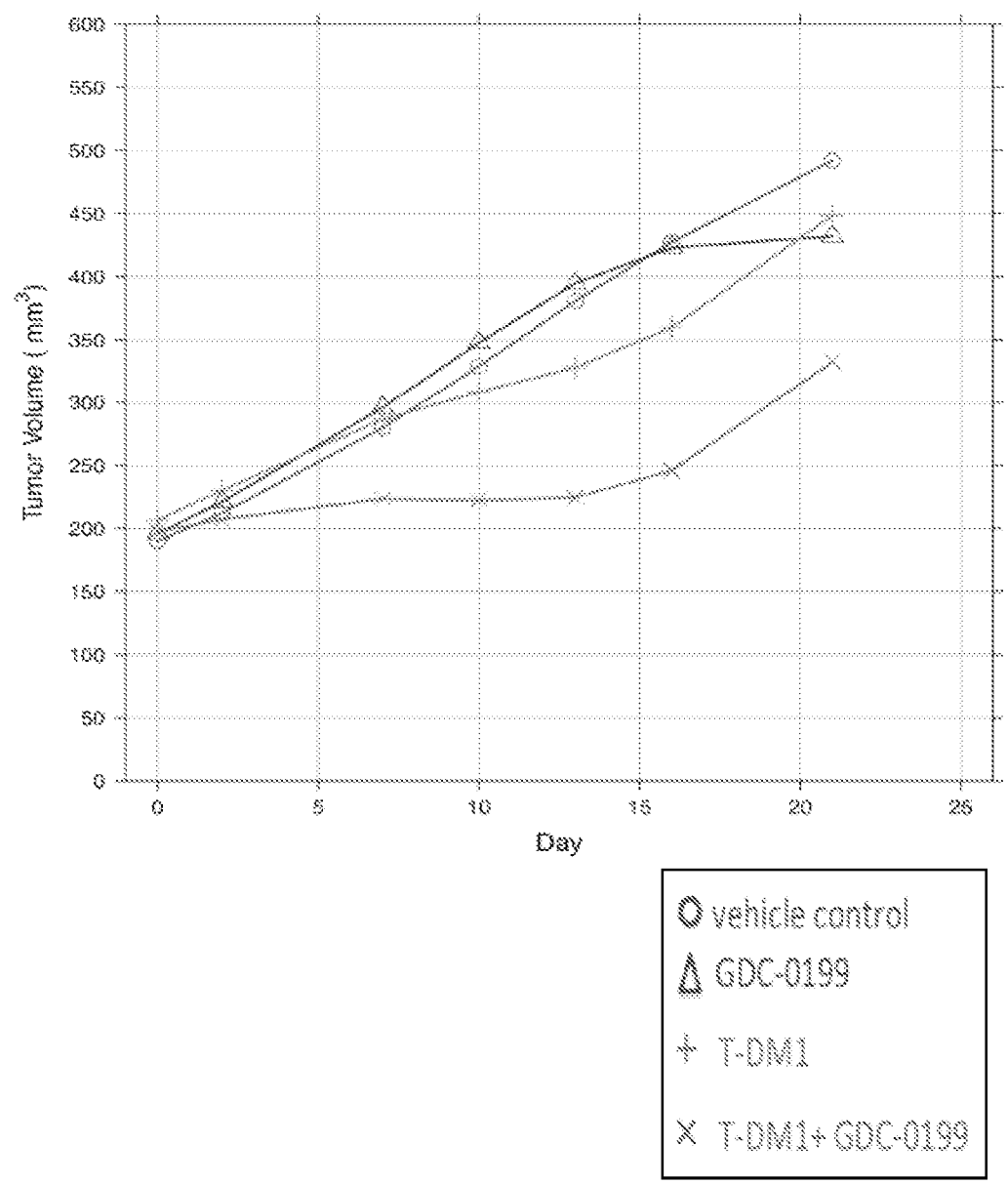
FIG. 5B shows the effect of T-DM1 (5 mg/kg administered once), GDC-0199 (100 mg/kg qd×21) or the combination on tumor growth (as measured by tumor volume) of Clone #17 T-DM1 resistant KPL-4 human breast cancer xenografts in SCID beige mice. Combination drug treatment resulted in tumor stasis, with no activity of single agent treatment.
Figure 6C:
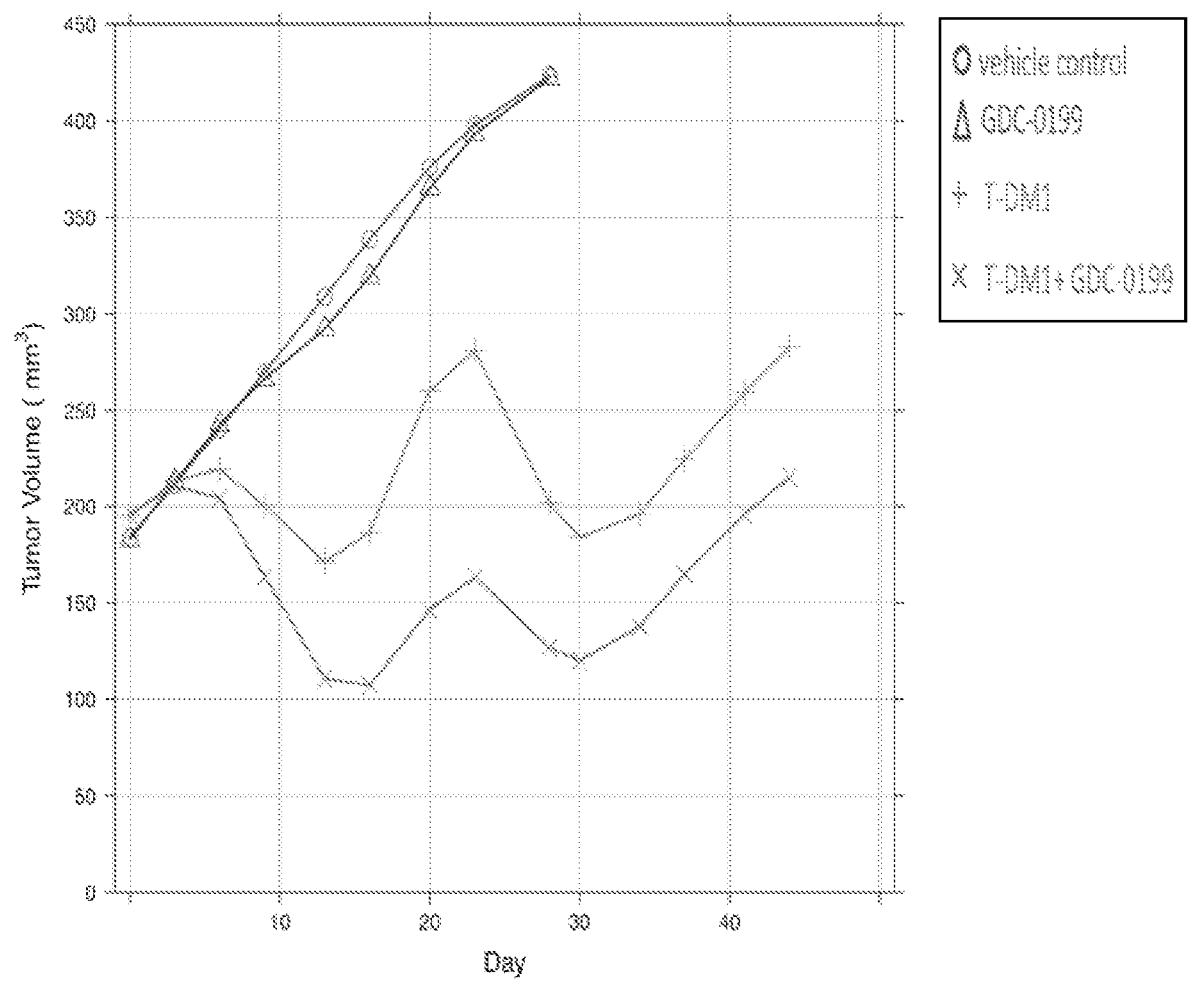
FIG. 6C shows the effect of T-DM1 (5 mg/kg q3w×2), GDC-0199 (100 mg/kg qd×21) or the combination on tumor growth (as measured by tumor volume) of Clone #8 T-DM1 resistant KPL-4 human breast cancer xenografts in SCID beige mice.

For all xenograft studies, three million T-DM1-resistant KPL-4 breast cancer cells were implanted in #2/3 mammary fat pads of female SCID-beige mice. When tumors reached a volume of approximately 200 $mm^3$, mice were randomized into treatment groups (n=10 mice pre group): 5 mg/kg T-DM1 q3w, 100 mg/kg GDC-0199 qd, combination of the two or vehicle. The results of these xenograft studies for xenografts of various clones of the T-DM1-resistant KPL-4 breast cancer cells are shown in FIGS. 5B and 6C. The results indicate enhanced anti-tumor effect when T-DM1 and GDC-0199 were used in combination, relative to single agent activity.

Example 5

IHC Studies—T-DM1-Resistant KPL-4 Xenograft Tumors

FFPE (formalin-fixed paraffin-embedded) xenograft tumors were sectioned for analysis of Bcl-2 and HER2 (ErbB2) expression by immunohistochemistry (IHC), using DAB detection method. Bcl-2 antibody SP66 was obtained from Ventana. Human tonsil sections served as Bcl-2 positive controls. Anti-HER2 antibody 4D5 was obtained from Ventana. Human breast cancer cell lines served as positive controls (SK-BR-3 as 3+; MDA-MB-361 as 2+; MBA-MB-231 as negative).

FIG. 7A shows the expression of Bcl-2 in formalin-fixed paraffin-embedded T-DM1-resistant KPL-4 xenograft tumor samples (Clones #8 and #17) determined by immunohistochemistry (IHC), using DAB detection method, as described above.

FIG. 7B shows the expression of HER2 (ErbB2) in formalin-fixed paraffin-embedded T-DM1-resistant KPL-4 xenograft tumor samples (Clones #8 and #17) determined by immunohistochemistry (IHC), using DAB detection method, as described above.

Anti-Bcl-2 antibody results: Vehicle groups of each clone showed similar low frequency of Bcl-2 reactive cells, most often located at the perimeter of tumor lobules (not shown). The frequency and intensity of the Bcl-2 signal at the tumor lobule margins in the T-DM1 treated groups was increased or not changed.

Anti-HER2 antibody results: Vehicle and T-DM1 treated tumors in all clones showed very high frequency of HER2 3+ IHC. In some T-DM1 treated tumors, there were regions of weaker HER2 staining (clone #17), most often adjacent to the stromal bands surrounding the tumor lobules (not shown).

The Bcl-2 IHC results demonstrate that Bcl-2 expression is maintained in the T-DM1 resistant clones #8 and #17 when grown as xenograft tumors (FIG. 7A; see also Example 6 which shows very little Bcl-2 expression in KPL-4 parental cells by Western blot). Bcl-2 expression in T-DM1-treated clone #17 is higher than the corresponding vehicle control. FIG. 7B depicts HER2 expression as assessed by IHC. In contrast to the relatively lower HER2 expression observed in cells grown in vitro, clones #8 and #17, in both vehicle and T-DM1-treated tumors, show high HER2 expression at the 2+ and 3+ level. All clone #8 tumors were determined to be 85-95% HER2+ or 3+, with a very low frequency of 2+ or 1+ tumor cells. Clone #17 tumors were more variable, with 35-75% HER2 3+ cells and 20-65% cells HER2 2+ in the vehicle group.

Example 6

Xenograft Studies—KPL-4 T-DM1-Resistant Breast Tumors

Figure 8:
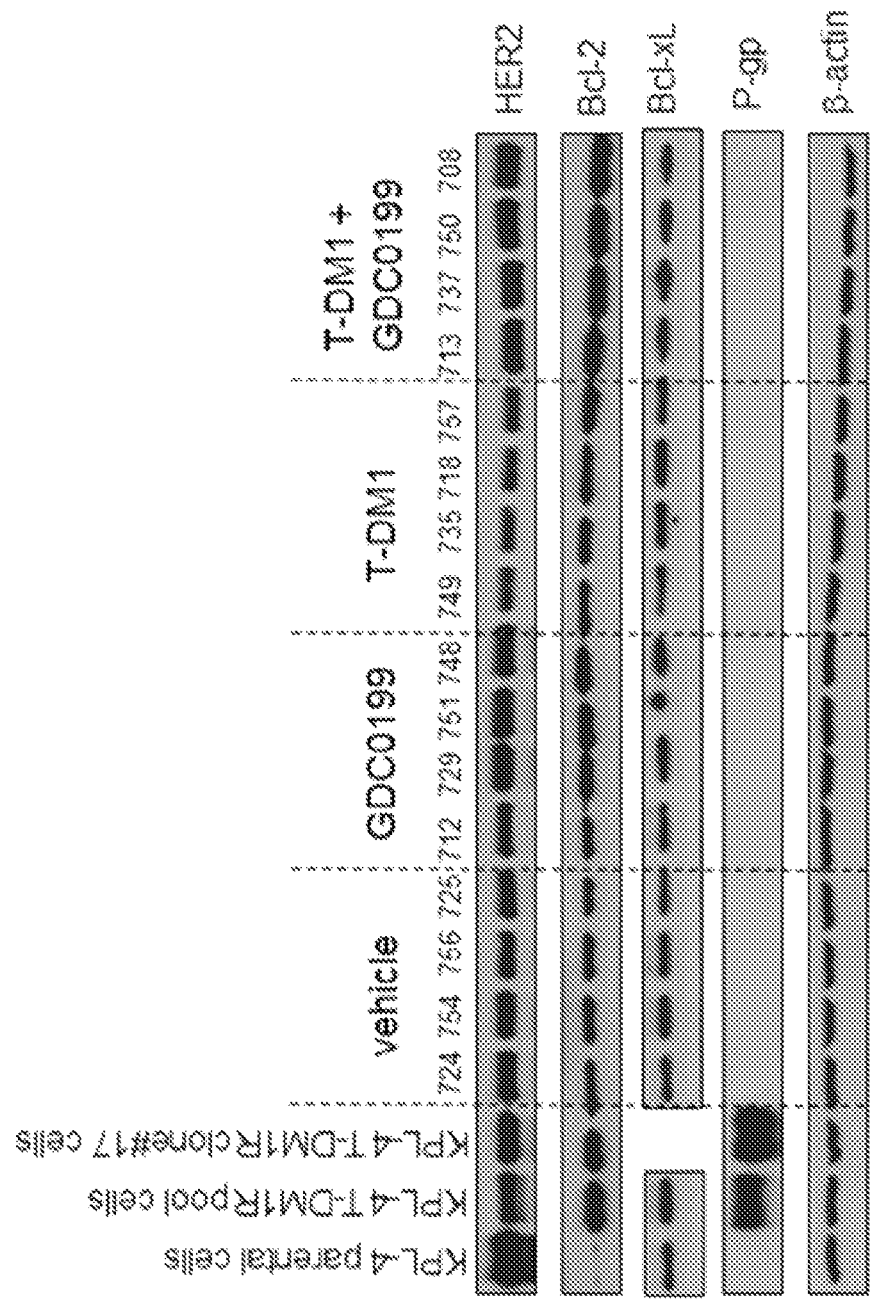
FIG. 8 shows protein expression as measured by Western blot analysis of Bcl-2 and HER2 in Clone #17 KPL-4 T-DM1-resistant xenograft tumors, treated with GDC-0199, T-DM1 or T-DM-1+ GDC-0199.

FIG. 8 shows Western blot expression data of Bcl-2, HER2, Bcl-xL and Pgp in KPL-4 T-DM1-resistant clone #17 xenograft tumors treated with GDC-0199, T-DM1 or T-DM-1+ GDC-0199. (The three digit numbers above lanes 4-19 indicated individual xenograft tumors.) The expression data show that HER2 and Bcl-2 expression are maintained in all groups, as compared to the corresponding cells grown in vitro in cell culture.

Example 7

Caspase 3/7 Luminescence and Fluorescence Activation Assays—T-DM1-Sensitive Breast Cancer Cell Lines Caspase 3/7 activation luminescence assay was performed as described in Example 3.

The caspase 3 activation fluorescence in vitro apoptosis assay was performed using IncuCyte™ reagents and equipment to measure caspase activation over time (kinetic analysis) essentially following manufacturing instructions.

Figure 9A:
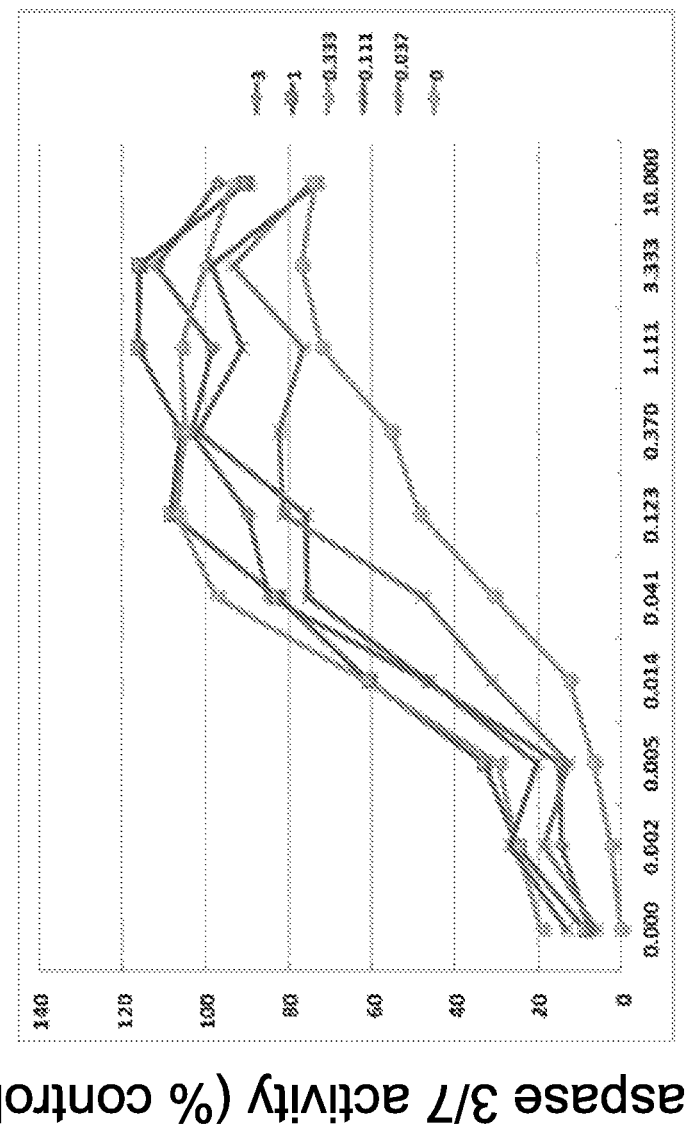
FIG. 9A presents results of a caspase 3/7 activation luminescent in vitro apoptosis assay, testing the effect of five separate concentrations of GDC-0199 (µM) in combination with 9 different concentrations of T-DM1 after 24 hours of treatment in HER2+ MDA-MB-361 breast cancer cells (T-DM1 naïve cells). The results demonstrate enhanced apoptosis greater than T-DM1 alone with all combinations tested.

FIG. 9A presents results of a caspase 3/7 luminescence in vitro apoptosis assay, testing the effect of five separate concentrations of GDC-0199 (μM) in combination with 9 different concentrations of T-DM1 on caspase activity in HER2+ MDA-MB-361 breast cancer cells, which are sensitive to T-DM1 (naive). The results demonstrate caspases 3 and 7 activation with T-DM1 which is enhanced in a dose-dependent manner with increasing concentrations of GDC-0199.

Figure 9B:
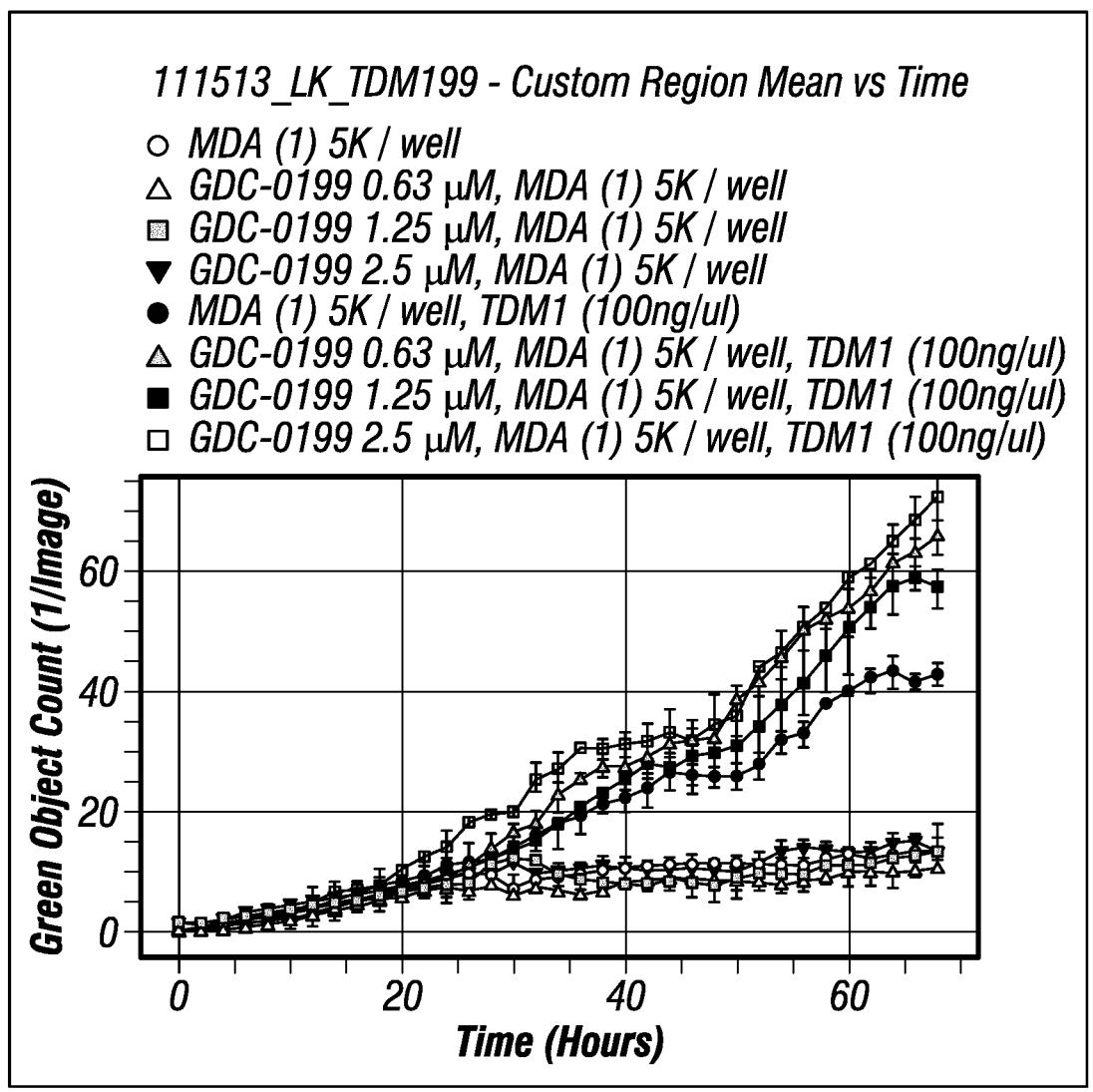
FIG. 9B presents the results of a kinetic caspase 3/7 activation fluorescent in vitro apoptosis assay, testing the effect of three different concentrations of GDC-0199 (0.63 µM, 1.25 µM, 2.5 µM), alone and in combination with T-DM1 (0.1 µg/mL), in HER2+ MDA-MB-361 breast cancer cells. The results demonstrate enhanced caspase activation greater than T-DM1 alone with all combinations tested.

FIG. 9B presents the results of a caspase 3 fluorescence in vitro apoptosis assay, testing the effect of three different concentrations of GDC-0199 (0.63 μM, 1.25 μM, 2.5 μM), alone and in combination with T-DM1 (0.1 μg/mL), on caspase activity in HER2+T-DM1 sensitive (naive) MDA-MB-361 breast cancer cells. The results demonstrate that GDC-0199 enhances caspase activation above that induced by T-DM1 alone in a dose- and time-dependent manner, and therefore results in enhanced apoptosis with all combinations.

FIG. 10A presents the results of a caspase 3/7 luminescence in vitro apoptosis assay, testing the effect of five separate concentrations of GDC-0199 (μM) in combination with 9 different concentrations of T-DM1 on caspase activity in T-DM1 naive HER2+ HCC1569 breast cancer cells. The results demonstrate that T-DM1 alone does not induce apoptosis but addition of GDC-0199 results in enhanced caspase activity and hence enhanced apoptosis in all combinations.

FIG. 10B presents the results of a caspase 3 fluorescence in vitro apoptosis assay, testing the effect of three different concentrations of GDC-0199 (0.63 μM, 1.25 μM, 2.5 μM), alone and in combination with T-DM1 (0.1 μg/mL), on caspase activity in HER2+ HCC1569 breast cancer cells. The results demonstrate that GDC-0199 enhances caspase activation above that induced by T-DM1 alone in a dose- and time-dependent manner, and therefore results in enhanced apoptosis with all combinations.

These results show that the T-DM1/GDC-0199 combination is also effective in T-DM1 naive (i.e. not T-DM1 resistant) cell lines.

Example 8

Xenograft Studies—TDM-1-Sensitive (naive) MDA-MB-361 Breast Tumors

Ten million MDA-MB-361 breast cancer cells were implanted into the right mammary fat pad of female NOD/SCID mice one day after implantation of 60-day release 1713-estradiol pellets. When tumors reached a volume of approximately 200-300 mm$^3$, mice were randomized into treatment groups (n=10 mice per group) and administered T-DM1 (1, 3, or 7 mg/kg i.v. once), GDC-0199 (100 mg/kg qd×21) or a combination of T-DM1 and GDC-0199 as shown in FIG. 11. The results indicate enhanced anti-tumor activity of GDC-0199 with 7 mg/kg T-DM1, relative to single agent activity.

Example 9

Western Analysis: Effects of T-DM1+/− GDC-0199 on Bcl-2 Family Member Proteins in HER2+ Breast Cancer Cell Lines The effect of treatment with T-DM1 (1.25 μg/mL) alone or in combination with GDC-0199 (1.25 μM) was studied on various T-DM1 naive HER2+ breast cancer cell lines. The results are shown in FIG. 12. Four out of the eight HER2+ breast cancer cell lines tested (BT-474, HCC1569, MDA-361 and ZR-75-30) expressed Bcl-2; all eight breast cancer cell lines expressed the other Bcl-2 family members assessed-Bcl-xL and Mcl-1. Three of the cell lines (BT-474, MDA_361 and ZR-75-30) showed phosphorylation of Bcl-2 after T-DM1 treatment, a known effect of exposure to anti-mitotic agents such as T-DM1. As shown in FIGS. 9A, 9B, 10A and 10B, MDA-MB-361 and HCC1569 showed enhanced apoptosis when treated with a combination of T-DM1 and GDC-0199.

T-DM1 (KADCYLA®) exhibits significant clinical benefits in the treatment of cancer for patients, such as breast cancer patients, who have progressed on prior HER2-targeted therapies, such as on treatment with trastuzumab (HERCEPTIN®). The U.S. Food and Drug Administration approved KADCYLA® (ado-trastuzumab emtansine), for the treatment of patients with HER2-positive, metastatic breast cancer who previously received treatment with trastuzumab and a taxane. The data presented here demonstrate that combination treatment with a Bcl (e.g. Bcl-2) inhibitor and T-DM1 significantly improves the efficacy of T-DM1 administered as a single agent. The results also demonstrate that such combination treatment with T-DM1 and a Bcl-2 inhibitor is effective both in the treatment of T-DM1 sensitive (naive) HER2 positive cancers (e.g. breast cancers) and HER2 positive cancers (e.g. breast cancers) resistant to treatment with T-DM1.

All publications and patent applications cited in this specification are herein incorporated by reference as if each individual publication or patent application were specifically and individually indicated to be incorporated by reference. Although the foregoing invention has been described in some detail by way of illustration and examples for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for the treatment of a HER2 positive cancer in a human in need thereof comprising administering to said human an effective amount of trastuzumab-MCC-DM1 and a selective Bcl-2 inhibitor, wherein the selective Bcl-2 inhibitor is 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof.

2. The method of claim 1, wherein the cancer is HER2 positive breast cancer or gastric cancer.

3. The method of claim 2, wherein the HER2-positive breast cancer or gastric cancer has an immunohistochemistry (IHC) score of 2+ or 3+ and/or an in situ hybridization (ISH) amplification ratio >2.0.

4. The method of claim 1, wherein the HER2 positive cancer is resistant to treatment with said trastuzumab-MCC-DM1 administered as a single agent.

5. The method of claim 1, wherein the HER2 positive cancer is sensitive to treatment with said trastuzumab-MCC-DM1 administered as a single agent.

6. The method of claim 1, wherein said trastuzumab-MCC-DM1 and said selective Bcl-2 inhibitor are (i) co-administered, (ii) administered simultaneously, (iii) administered consecutively, (iv) administered in a combined formulation or (v) administered in alternation.

* * * * *

SEQUENCE LISTING

<160> NUMBER OF SEQ ID NOS: 2

<210> SEQ ID NO 1
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

-continued

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```